United States Patent
Lee et al.

(10) Patent No.: US 9,512,235 B2
(45) Date of Patent: Dec. 6, 2016

(54) RNA-SPECIFIC BINDING ANTIBODY

(71) Applicant: KOREA ADVANCED INSTITUTE OF SCIENCE AND TECHNOLOGY, Daejeon (KR)

(72) Inventors: Younghoon Lee, Daejeon (KR); Euihan Jung, Yongin-si (KR); Jung Min Lee, Yongin-si (KR); Insoo Park, Goyang-si (KR); Hyo Jeong Hong, Chuncheon-si (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 80 days.

(21) Appl. No.: 14/302,559

(22) Filed: Jun. 12, 2014

(65) Prior Publication Data
US 2015/0266975 A1    Sep. 24, 2015

(30) Foreign Application Priority Data
Mar. 18, 2014  (KR) .......................... 10-2014-0031768

(51) Int. Cl.
| | | |
|---|---|---|
| C07K 16/18 | (2006.01) | |
| G01N 33/53 | (2006.01) | |
| C07K 16/44 | (2006.01) | |
| C12Q 1/68 | (2006.01) | |

(52) U.S. Cl.
CPC ............ C07K 16/44 (2013.01); C12Q 1/6804 (2013.01); *C07K 2317/21* (2013.01); *C07K 2317/55* (2013.01); *C07K 2317/565* (2013.01); *C07K 2317/92* (2013.01)

(58) Field of Classification Search
CPC . C07K 16/44; C07K 2317/76; C07K 2317/21; C07K 2317/565; C07K 2317/34
See application file for complete search history.

(56) References Cited

U.S. PATENT DOCUMENTS 5,670,318 A * 9/1997 Tiedge ................ C12Q 1/6883
435/6.14
2008/0069822 A1 3/2008 Jensen

OTHER PUBLICATIONS

Buneva VN et al. Natural antibodies to nucleic acids. Biochemistry (Moscow), 2013, 78(2):127-143.*
Chen W et al. Expression of neural BC200 RNA in human tumours. J. Pathol. 1997, 183:345-351.*
Doerr A. RNA antibodies: upping the ante. Nat. Methods, 2008, 5(3):220.*
Uchiumi T et al. A human autoantibody specific for a unique conserved region of 28 S ribosomal RNA inhibits the interaction of elongation factors 1 alpha and 2 with ribosomes. J. Biol. Chem. 266(4):2054-2062.*
Ye J-D et al. Synthetic antibodies for specific recognition and crystallization of structured RNA. Proc. Natl. Acad. Sci. USA, 2008, 105(1):82-87.*

* cited by examiner

*Primary Examiner* — Kimberly A. Ballard
(74) *Attorney, Agent, or Firm* — Lex IP Meister, PLLC

(57) ABSTRACT

The present invention relates to an antibody being capable of binding specifically to BC200 RNA or its antigen binding fragment, a polynucleotide of encoding the antibody or its antigen binding fragment, a composition, kit and method for detecting BC200 RNA in a sample using the antibody or its antigen binding fragment, and a composition for diagnosis, prevention or treatment of BC200 RNA-associated diseases including the antibody or its antigen binding fragment.

12 Claims, 26 Drawing Sheets
(12 of 26 Drawing Sheet(s) Filed in Color)

FIG. 6

| Clone | $K_d$ (nM) | CDR-L3 | CDR-H1 | CDR-H2 | CDR-H3 |
|---|---|---|---|---|---|
| MabBC200-A | ~36 | QQSYS--FPWT | GYTLSAYY | INPRGGRT | AAARGSPRSRFYYGMGV |
| MabBC200-B | ~76 | ATWDDSRNGLV | GYTLSTYY | INSRGGRT | ARGSPRLRRDPRRAFDI |

FIG. 10

| Clone | $K_d$ (nM) | CDR-L3 | Fold enhancement |
|---|---|---|---|
| MabBC200-A | ~36 | Q Q S Y S F P W T | - |
| MabBC200-A1 | ~11 | Q Q G Y S F P W T | 3.3 |
| MabBC200-A2 | ~15 | Q Q A Y S F P W T | 2.4 |
| MabBC200-A3 | ~7 | Q Q C Y S F P W T | 5.1 |
| MabBC200-A4 | ~18 | Q Q V Y S F P W T | 2 |

SEQUENCE LISTING

```
<160> NUMBER OF SEQ ID NOS: 35

<210> SEQ ID NO 1
<211> LENGTH: 8
<212> TYPE: PRT
<213> ORGANISM: Artificial Sequence
<220> FEATURE:
<223> OTHER INFORMATION: MabBC200-A Heavy Chain CDR1

<400> SEQUENCE: 1

Gly Tyr Thr Leu Ser Ala Tyr Tyr
  1               5

<210> SEQ ID NO 2
<211> LENGTH: 8
<212> TYPE: PRT
<213> ORGANISM: Artificial Sequence
<220> FEATURE:
<223> OTHER INFORMATION: MabBC200-A Heavy Chain CDR2

<400> SEQUENCE: 2

Ile Asn Pro Arg Gly Gly Arg Thr
  1               5

<210> SEQ ID NO 3
<211> LENGTH: 18
<212> TYPE: PRT
<213> ORGANISM: Artificial Sequence
<220> FEATURE:
<223> OTHER INFORMATION: MabBC200-A Heavy Chain CDR3

<400> SEQUENCE: 3

Cys Ala Ala Arg Gly Ser Pro Arg Ser Arg Phe Tyr Tyr Gly Met Gly
```

```
                1               5                  10                  15
Val Trp

<210> SEQ ID NO 4
<211> LENGTH: 6
<212> TYPE: PRT
<213> ORGANISM: Artificial Sequence
<220> FEATURE:
<223> OTHER INFORMATION: MabBC200-A Light Chain CDR1

<400> SEQUENCE: 4

Gln Ser Ile Asn Asn Tyr
  1               5

<210> SEQ ID NO 5
<211> LENGTH: 3
<212> TYPE: PRT
<213> ORGANISM: Artificial Sequence
<220> FEATURE:
<223> OTHER INFORMATION: MabBC200-A Light Chain CDR2

<400> SEQUENCE: 5

Ala Thr Ser
  1

<210> SEQ ID NO 6
<211> LENGTH: 11
<212> TYPE: PRT
<213> ORGANISM: Artificial Sequence
<220> FEATURE:
<223> OTHER INFORMATION: MabBC200-A Light Chain CDR3

<400> SEQUENCE: 6

Cys Gln Gln Ser Tyr Ser Phe Pro Trp Thr Phe
  1               5                  10

<210> SEQ ID NO 7
<211> LENGTH: 11
<212> TYPE: PRT
<213> ORGANISM: Artificial Sequence
<220> FEATURE:
<223> OTHER INFORMATION: MabBC200-A1 Light Chain CDR3

<400> SEQUENCE: 7

Cys Gln Gln Gly Tyr Ser Phe Pro Trp Thr Phe
  1               5                  10

<210> SEQ ID NO 8
<211> LENGTH: 11
<212> TYPE: PRT
<213> ORGANISM: Artificial Sequence
<220> FEATURE:
<223> OTHER INFORMATION: MabBC200-A2 Light Chain CDR3

<400> SEQUENCE: 8

Cys Gln Gln Ala Tyr Ser Phe Pro Trp Thr Phe
  1               5                  10

<210> SEQ ID NO 9
<211> LENGTH: 11
<212> TYPE: PRT
<213> ORGANISM: Artificial Sequence
<220> FEATURE:
<223> OTHER INFORMATION: MabBC200-A3 Light Chain CDR3

<400> SEQUENCE: 9
```

```
Cys Gln Gln Cys Tyr Ser Phe Pro Trp Thr Phe
 1               5                   10
```

<210> SEQ ID NO 10
<211> LENGTH: 11
<212> TYPE: PRT
<213> ORGANISM: Artificial Sequence
<220> FEATURE:
<223> OTHER INFORMATION: MabBC200-A4 Light Chain CDR3

<400> SEQUENCE: 10

```
Cys Gln Gln Val Tyr Ser Phe Pro Trp Thr Phe
 1               5                   10
```

<210> SEQ ID NO 11
<211> LENGTH: 10
<212> TYPE: RNA
<213> ORGANISM: Artificial Sequence
<220> FEATURE:
<223> OTHER INFORMATION: BC200 RNA 76-85 position

<400> SEQUENCE: 11
ggaguucgag                                                            10

<210> SEQ ID NO 12
<211> LENGTH: 9
<212> TYPE: RNA
<213> ORGANISM: Artificial Sequence
<220> FEATURE:
<223> OTHER INFORMATION: BC200RNA 96-104 position

<400> SEQUENCE: 12 gcaauauag                                                              9

<210> SEQ ID NO 13
<211> LENGTH: 200
<212> TYPE: RNA
<213> ORGANISM: Human

<400> SEQUENCE: 13
ggccgggcgc gguggcucac gccuguaauc ccagcucuca gggaggcuaa gaggcgggag     60
gauagcuuga gcccaggagu ucgagaccug ccugggcaau auagcgagac cccguucucc    120
agaaaaagga aaaaaaaaaa caaaagacaa aaaaaaaaua agcguaacuu cccucaaagc    180
aacaaccccc cccccccuuu                                                200

<210> SEQ ID NO 14
<211> LENGTH: 46
<212> TYPE: RNA
<213> ORGANISM: Artificial Sequence
<220> FEATURE:
<223> OTHER INFORMATION: adaptor RNA

<400> SEQUENCE: 14
ggaucgcauu uggacuucug cccgcaaggg caccacgguc ggaucc                    46

<210> SEQ ID NO 15
<211> LENGTH: 21
<212> TYPE: DNA
<213> ORGANISM: Artificial Sequence
<220> FEATURE:
<223> OTHER INFORMATION: Biotin oligonucleotide

<400> SEQUENCE: 15
aggatccgac cgtggtgccc t                                               21

<210> SEQ ID NO 16
<211> LENGTH: 37
<212> TYPE: DNA
<213> ORGANISM: Artificial Sequence
<220> FEATURE:
<223> OTHER INFORMATION: T7-BC200-Fwd

<400> SEQUENCE: 16
gaattctaat acgactcact ataggccggg cgcggtg                      37

<210> SEQ ID NO 17
<211> LENGTH: 66
<212> TYPE: DNA
<213> ORGANISM: Artificial Sequence
<220> FEATURE:
<223> OTHER INFORMATION: Biotin-StuI-Rev

<400> SEQUENCE: 17
cttccggatc cgaccgtggt gcccttgcgg gcagaagtcc aaatgcgatc caaagggggg    60
gggggg                                                               66

<210> SEQ ID NO 18
<211> LENGTH: 18
<212> TYPE: DNA
<213> ORGANISM: Artificial Sequence
<220> FEATURE:
<223> OTHER INFORMATION: Primer H

<400> SEQUENCE: 18
gcgaagtcac ccatcagg                                           18

<210> SEQ ID NO 19
<211> LENGTH: 18
<212> TYPE: DNA
<213> ORGANISM: Artificial Sequence
<220> FEATURE:
<223> OTHER INFORMATION: PrimerL

<400> SEQUENCE: 19
tagctcactc attaggca                                           18

<210> SEQ ID NO 20
<211> LENGTH: 18
<212> TYPE: DNA
<213> ORGANISM: Artificial Sequence
<220> FEATURE:
<223> OTHER INFORMATION: Uni-HC_PCR1-Up

<400> SEQUENCE: 20
ccggaattca ctctaacc                                           18

<210> SEQ ID NO 21
<211> LENGTH: 24
<212> TYPE: DNA
<213> ORGANISM: Artificial Sequence
<220> FEATURE:
<223> OTHER INFORMATION: A-HC_PCR1-Dn

<400> SEQUENCE: 21
gaacctggga gaggacacct gtag                                    24

<210> SEQ ID NO 22
<211> LENGTH: 23
<212> TYPE: DNA

```
<213> ORGANISM: Artificial Sequence
<220> FEATURE:
<223> OTHER INFORMATION: A-HC_PCR2-Up

<400> SEQUENCE: 22
cctctcccag gttcagctgg tgc                                          23

<210> SEQ ID NO 23
<211> LENGTH: 20
<212> TYPE: DNA
<213> ORGANISM: Artificial Sequence
<220> FEATURE:
<223> OTHER INFORMATION: Uni-HC_PCR2-Dn

<400> SEQUENCE: 23
cgatgggccc ttggccgtgc                                              20

<210> SEQ ID NO 24
<211> LENGTH: 24
<212> TYPE: DNA
<213> ORGANISM: Artificial Sequence
<220> FEATURE:
<223> OTHER INFORMATION: B-HC_PCR1-Dn

<400> SEQUENCE: 24
gcatttggga gaggacacct gtag                                         24

<210> SEQ ID NO 25
<211> LENGTH: 23
<212> TYPE: DNA
<213> ORGANISM: Artificial Sequence
<220> FEATURE:
<223> OTHER INFORMATION: B-HC_PCR2-Up

<400> SEQUENCE: 25
cctctcccaa atgcagctgg tgc                                          23

<210> SEQ ID NO 26
<211> LENGTH: 22
<212> TYPE: DNA
<213> ORGANISM: Artificial Sequence
<220> FEATURE:
<223> OTHER INFORMATION: A-LC_PCR1_Up

<400> SEQUENCE: 26
gaaggagata ttgtgatgac cc                                           22

<210> SEQ ID NO 27
<211> LENGTH: 15
<212> TYPE: DNA
<213> ORGANISM: Artificial Sequence
<220> FEATURE:
<223> OTHER INFORMATION: A-LC_PCR2_Up

<400> SEQUENCE: 27
cacaatatct ccttc                                                   15

<210> SEQ ID NO 28
<211> LENGTH: 16
<212> TYPE: DNA
<213> ORGANISM: Artificial Sequence
<220> FEATURE:
<223> OTHER INFORMATION: Uni-LC_PCR2_Dn

<400> SEQUENCE: 28
cccaagcttc ggcacg                                                  16
```

<210> SEQ ID NO 29
<211> LENGTH: 29
<212> TYPE: DNA
<213> ORGANISM: Artificial Sequence
<220> FEATURE:
<223> OTHER INFORMATION: B-LC_PCR1_Dn

<400> SEQUENCE: 29
agccaccgta cgtaggacgg tcagcttgg                                    29

<210> SEQ ID NO 30
<211> LENGTH: 22
<212> TYPE: DNA
<213> ORGANISM: Artificial Sequence
<220> FEATURE:
<223> OTHER INFORMATION: B-LC_PCR1_Up

<400> SEQUENCE: 30
gaaggacagt ctgtgctgac gc                                           22

<210> SEQ ID NO 31
<211> LENGTH: 26
<212> TYPE: DNA
<213> ORGANISM: Artificial Sequence
<220> FEATURE:
<223> OTHER INFORMATION: B-LC_PCR2_Up

<400> SEQUENCE: 31
gcacagactg tccttcaaca ccagac                                       26

<210> SEQ ID NO 32
<211> LENGTH: 44
<212> TYPE: DNA
<213> ORGANISM: Artificial Sequence
<220> FEATURE:
<223> OTHER INFORMATION: RNA(51-120)-T7-up

<400> SEQUENCE: 32
ccggaattct aatacgactc actataggga ggcgggagga tagc                   44

<210> SEQ ID NO 33
<211> LENGTH: 24
<212> TYPE: DNA
<213> ORGANISM: Artificial Sequence
<220> FEATURE:
<223> OTHER INFORMATION: RNA(51-120)-T7-dn

<400> SEQUENCE: 33
tcccccggga gaacggggtc tcgc                                         24

<210> SEQ ID NO 34
<211> LENGTH: 30
<212> TYPE: DNA
<213> ORGANISM: Artificial Sequence
<220> FEATURE:
<223> OTHER INFORMATION: 7SL complementary oligonucleotide

<400> SEQUENCE: 34
gaggtcacca tattgatgcc gaacttagtg                                   30

<210> SEQ ID NO 35
<211> LENGTH: 22
<212> TYPE: DNA
<213> ORGANISM: Artificial Sequence
<220> FEATURE:

```
<223> OTHER INFORMATION: 5S complementary oligonucleotide

<400> SEQUENCE: 35
catccaagta ctaaccaggc cc                                                22
```

RNA-SPECIFIC BINDING ANTIBODY

CROSS-REFERENCE TO RELATED APPLICATION

This application claims the benefit of Korean Patent Application No. 10-2014-0031768, filed on Mar. 18, 2014, in the Korean Intellectual Property Office, the entire disclosure of which is incorporated herein by reference.

TECHNICAL FIELD

The present invention relates to an antibody being capable of binding specifically to BC200 RNA or its antigen binding fragment, a polynucleotide of encoding the antibody or its antigen binding fragment, a composition, kit and method for detecting BC200 RNA in a sample using the antibody or its antigen binding fragment, and a composition for diagnosis, prevention or treatment of BC200 RNA-associated diseases including the antibody or its antigen binding fragment.

RNA has various functions in a cell due to its secondary or tertiary structure, as well as a simple transferring material of genetic information. For performing various intracellular functions of RNA, RNA should have the secondary or tertiary structure required for the functions. The cell includes various RNA having different secondary or tertiary structure, although RNA has the same nucleotide sequence. However, the general method for analyzing RNA has adopted the hybridization method up to now, but cannot be used for analyzing RNA having the same nucleotide sequence but different secondary or tertiary structure, because the secondary or tertiary structure of RNA is not easy to be maintained under the hybridization condition.

As various functional RNA such as brain cytoplasmic 200 (BC200 RNA) becomes more important, the functional RNA should be analyzed absolutely. If an antibody recognizing the RNA structure is developed, it can be useful for understanding the basic concept of RNA-protein interaction occurred in a cell, analysis of the structural RNA function, a biochip or biosensor and the development of a diagnosing agent and a treating agent.

There are many efforts to search the RAN-binding, after the importance of RNA-binding antibody has been reported.

However, the antibody having a high affinity and specificity to the antigen RNA can be developed for a molecule recognizing the RNA structure, but cannot be prepared according to the conventional methods using animal. The reason is that RNA dissociates shortly after being injected into an animal due to the instability of RNA. In this context, there is scarcely any attempt to prepare an antibody recognizing the RNA structure. The antibody recognizing a certain molecular structure can be prepared in vitro by using a human antibody library which has been developed recently, and thus the human antibody library can be used for preparing a human antibody recognizing the RNA structure by overcoming the problems of RNA instability.

For examples, the methods of searching a RNA-binding antibody include a method of panning using a magnetic bead according to Jing-Dong Y., et al. (PNAS Vol. 105, No. 1, 82-87 (2007), Synthetic antibodies for specific recognition and crystallization of structured RNA). The panning method has some disadvantages in non-specificity of solution separation step due to the fluidity of magnetic bead, and a difficulty in selecting an antibody having a high affinity and specificity, when the bead is washed at the same number of times for the increased number of panning round. Because the method uses a synthetic library, it has a limited application. Any method of making up for the disadvantages has not been developed up to now.

The present inventors have researched continuously for searching a method of selecting a RNA-binding antibody, and an antibody binding specifically to and recognizing the functional structure of BC200 RNA (Korean patent application no. 10-2012-0155487).

SUMMARY OF THE INVENTION

An object of the present invention is to provide an antibody or its antigen binding fragment, which binds specifically to a region of $50^{th}$ nucleotide to $120^{th}$ nucleotide in the nucleotide sequence of a brain cytoplasmic 200 (BC200) RNA having SEQ ID NO: 13

An object of the present invention is to provide an antibody or its antigen binding fragment comprising a variable region of heavy chain (VH) comprising a complementarity determining region 1 (CDR1) consisting of an amino acid sequence of SEQ ID No: 1, CDR2 consisting of an amino acid sequence of SEQ ID NO: 2, and CDR3 consisting of an amino acid sequence of SEQ ID NO: 3; and a variable region of light chain (VL) comprising CDR1 consisting of an amino acid sequence of SEQ ID NO: 4, CDR2 consisting of an amino acid sequence of SEQ ID NO: 5, and CDR3 consisting of an amino acid sequence which Serine at fourth position in an amino acid of SEQ ID NO: 6 is substituted with other amino acid.

An object of the present invention is to provide an antibody or its antigen binding fragment which binds specifically to a region of $50^{th}$ nucleotide to $120^{th}$ nucleotide of a brain cytoplasmic 200 (BC200) RNA.

An object of the present invention is to provide a nucleic acid molecule comprising a nucleotide sequence encoding a complementarity determining region 3 (CDR3) of light chain ($V_L$) consisting of an amino acid sequence selected from the group consisting of amino acid sequences consisting of SEQ ID NO: 7 to SEQ ID NO: 10, or its complementary nucleotide sequence.

An object of the present invention is to provide a nucleic acid molecule comprising a nucleotide sequence encoding the antibody or its antigen binding fragment.

An object of the present invention is to provide a composition for detecting BC200 RNA comprising an antibody or its antigen binding fragment.

An object of the present invention is to provide a kit for detecting BC200 RNA comprising an antibody or its antigen binding fragment.

An object of the present invention is to provide a method of detecting BC200 RNA in a sample, comprising a step of reacting an antibody or its antigen binding fragment with the sample.

An object of the present invention is to provide a composition for diagnosing a disease associated with BC200 RNA, which comprises an antibody or its antigen binding fragment.

An object of the present invention is to provide a composition for preventing or treating a disease associated with BC200 RNA, which comprises an antibody or its antigen binding fragment.

An object of the present invention is to provide a method for preventing or treating a disease associated with BC200 RNA, which comprises administering an antibody or its antigen binding fragment to a subject in need.

DETAILED DESCRIPTION OF THE EMBODIMENTS

To carry out the objects of present invention, an embodiment of present invention relates to an antibody or its antigen binding fragment comprising:

a variable region of heavy chain (VH) comprising an complementarity determining region 1 (CDR1) consisting of an amino acid sequence of SEQ ID No: 1, CDR2 consisting of an amino acid sequence of SEQ ID NO: 2, and CDR3 consisting of an amino acid sequence of SEQ ID NO: 3; and a variable region of light chain (VL) comprising CDR1 consisting of an amino acid sequence of SEQ ID NO: 4, CDR2 consisting of an amino acid sequence of SEQ ID NO: 5, and CDR3 consisting of an amino acid sequence which serine at fourth position in an amino acid of SEQ ID NO: 6 is substituted with other amino acid.

Specifically, the CDR3 of variable region of light chain (VL) consists of an amino acid sequence which Serine at fourth position in an amino acid of SEQ ID NO: 6 is substituted with Glycine (G), Alanine (A), Cysteine (C) or Valine (V).

Another embodiment relates to an antibody or its antigen binding fragment antibody or its antigen binding fragment where the CDR3 of variable region of light chain ($V_L$) consists of an amino acid sequence of SEQ ID NO: 7.

An embodiment relates to an antibody or its antigen binding fragment antibody or its antigen binding fragment, where the CDR3 of variable region of light chain ($V_L$) consists of an amino acid sequence of SEQ ID NO: 8.

An embodiment relates to an antibody or its antigen binding fragment antibody or its antigen binding fragment, where the CDR3 of variable region of light chain ($V_L$) consists of an amino acid sequence of SEQ ID NO: 9.

An embodiment relates to an antibody or its antigen binding fragment antibody or its antigen binding fragment, where the CDR3 of variable region of light chain ($V_L$) consists of an amino acid sequence of SEQ ID NO: 10.

The antibody of present invention can be a complete antibody and its functional fragment. The whole antibody includes two full-length light chains and two full-length heavy chains where the light chain and the heavy chain are linked each other via the disulfide bond. The functional fragment of antibody means an antibody fragment maintaining the antigen-binding property, and the examples of fragment are (i) Fab fragment including a variable region of light chain ($V_L$), a variable region of heavy chain ($V_H$), a constant region of light chain ($C_L$) and a first constant region of heavy chain ($C_{H1}$); (ii) Fd fragment including $V_H$ domain and CH1 domain; (iii) Fv fragment including $V_L$ domain and $V_H$ domain of a single antibody; (iv) dAb fragment including $V_H$ domain; (v) separated CDR; (vi) F(ab')$_2$ fragment of two connected Fab fragment; (vii) single chain Fv molecule (scFv) including $V_H$ domain and $V_L$ domain linked by a peptide linker which can form the antigen binding region; (viii) Fv dimer including di-specific single Fv, (ix) diabody of multivalent or multi-specific fragment which can be prepared by gene fusion, and the like.

Herein, the term 'panning' means a process of selecting a specific phage expressing on its coat a peptide binding to target molecules such as antibody, enzyme, cell-surface receptor, from a phage library displaying a peptide on its coat.

The whole antibody includes two full-length light chains and two full-length heavy chains where the light chain and the heavy chain are linked each other via the disulfide bond. The constant regions of antibody are a constant region of heavy chain and a constant region of light chain. The heavy chain includes the classes of gamma (γ), μ, α, δ and ε types, and the subclasses of γ1, γ2, γ3, γ4, α1 and α2. The constant region of light chain includes κ and λ types.

Herein, the term "heavy chain" includes a full-length heavy chain having a variable domain of $V_H$ containing an amino acid sequence being capable of giving a sufficient antigen-binding specificity, three constant domains of CH1, CH2 and CH3, and a hinge, and a fragment of heavy chain. Herein, the term "light chain" includes a full-length light chain having a variable domain of $V_L$ containing an amino acid sequence being capable of giving a sufficient antigen-binding specificity and a constant domain of CL, and a fragment of light chain.

The term "CDR (complementarity determining region)" refers to an amino acid sequence of a hyper-variable region in a heavy chain and a light chain of immunoglobulin. The heavy chain and light chain can contain three CDRs respectively (CDRH1, CDRH2, CDRH3 and CDRL1, CDRL2, CDRL3). The CDR can give an important residue for contacting an antigen or epitope. The terms "specific binding" or "specific recognizing" are used as the same meanings known to an ordinarily-skilled person in the art, and means an immunological reaction of specific interaction between an antigen and an antibody.

In an embodiment, the antibody can include an antigen binding fragment selected from the group consisting of scFv, (scFv)$_2$, Fab, Fab' and F(ab')$_2$. The term, "antigen binding fragment" refers a fragment including an antigen-binding part of whole immunoglobulin, and for examples includes scFv, (scFv)$_2$, Fab, Fab' or F(ab')$_2$ but not limited thereto.

The antigen binding fragment can be obtained by using a protein hydrolyzing enzyme, for example Fab fragment obtained by cleaving the whole antibody with papain or F(ab')$_2$ fragment obtained by cleaving the whole antibody with pepsin, or by using recombinant gene technology.

Brain cytoplasmic 200 (BC200) was firstly discovered as non-coding RNA expressed specifically in a nerve cell (ncRNA) of a primate brain (Tiedge, H., et al., J Neurosci, 1993, Watson, J. B. and Sutcliffe, J. G., Mol Cell Biol, 1987), and was regarded as a local regulating factor for protein synthesis in neurodentrite (Lin, D., et al., Mol Cell Biol, 2008). In addition, BC200 RNA was expressed in various tumorous tissues derived different tissues such as well as nerve tissue, and particularly, BC200 RNA was expressed at a higher degree in metastatic breast cancer rather than a benign breast cancer (Chen, W., et al., J Pathol, 1997 및 Iacoangeli, A., et al., Carcinogenesis, 2004). The expression of BC200 RNA has been reported in the neurological disease such as Alzheimer's disease (Lukiw, W. J., et al., Neurochem Res, 1992, Mus, E., et al., Proc Natl Acad Sci USA, 2007). The BC200 RNA contains a nucleotide sequence of SEQ ID NO: 13, or preferably consists of a nucleotide sequence of SEQ ID NO: 13.

An embodiment of the present invention relates to an antibody or its antigen binding fragment which binds specifically to a region of $50^{th}$ nucleotide to $120^{th}$ nucleotide as shown in SEQ ID NO: 13 of BC200 RNA, or more specifically, a region of SEQ ID NO: 11 or SEQ ID NO: 12 in nucleotide sequence of BC200 RNA.

An embodiment of the present invention relates to a nucleic acid molecule comprising a nucleotide sequence encoding a complementarity determining region 3 (CDR3) of light chain ($V_L$) consisting of an amino acid selected from the group consisting of amino acid sequences consisting of SEQ ID NO: 7 to SEQ ID NO: 10, or its complementary nucleotide sequence.

In addition, an embodiment provides a nucleic acid molecule comprising a nucleotide sequence encoding an antibody or its antigen binding fragment, where the antibody comprising:

a variable region of heavy chain (VH) comprising an complementarity determining region 1 (CDR1) consisting of an amino acid sequence of SEQ ID No: 1, CDR2 consisting of an amino acid sequence of SEQ ID NO: 2, and CDR3 consisting of an amino acid sequence of SEQ ID NO: 3; and, a variable region of light chain (VL) comprising CDR1 consisting of an amino acid sequence of SEQ ID NO: 4, CDR2 consisting of an amino acid sequence of SEQ ID NO: 5, and CDR3 consisting of an amino acid sequence which Serine at fourth position in an amino acid of SEQ ID NO: 6 is substituted with other amino acid.

An embodiment of the present invention relates to a composition for detecting BC200 RNA, or diagnosing a disease associated with BC200 RNA, which comprises an antibody or its antigen binding fragment.

Besides the antibody specific to BC200 RNA, any agent which has been used for immunological analysis can be contained in the composition. The examples of agents are a detectable labeling agent, a solubilizing agent, and a washing agent.

Any immunological analysis can be adopted, as long as it can detect the antigen-antibody reaction. The immunological analysis has been well-known in the art, and for examples, includes immunocytochemistry, immunohistochemistry, radioimmunoassays, Enzyme Linked Immunoabsorbent assay (ELISA), immunoblotting, Farr assay, immunoprecipitation, Latex agglutination, hemagglutination, turbidimetry, immunodiffusion, counter immunoelectrophoresis, single radial immunodiffusion, immunochromatography, protein chip and immunofluorescence.

In case of the enzyme used as a labeling agent, the composition further includes a substrate and a reaction quencher. The detectable labeling agent can be a material being capable of detecting an antigen-antibody complex quantitatively or qualitatively and for examples includes enzyme, fluorescent material, ligand, luminescent material, microparticle, redox molecule and radioactive material. The examples of enzyme are β-glucuronidase, β-D-glucosidase, urease, peroxidase, alkaline phosphatase, acetylcholine esterase, glucose oxidase, hexokinase, maleate dehydrogenase, glucose-6-phosphoric acid dehydrogenase, invertase and the like. The examples of fluorescent material are fluorescein, isothiocyanate, rhodamine, phycoerythrin, phycocyanin, allophycocyanin, fluorescinisothiocyanate and the like. As a ligand, there are biotin derivatives and acridium, ester, luciferin and luciferase as a luminous material. As a microparticle, there are colloid gold and colored latex, and as a redox molecule, there are ferrocene, ruthenium complex compound, biologen, quinone, Ti ion, Cs ion, dimide, 1,4-benzoquinone and hydroquinone. As a radioactive isotope, $^3$H $^{14}$C, $^{32}$P $^{35}$S, $^{36}$Cl, $^{51}$Cr, $^{57}$Co, $^{58}$Co, $^{59}$Fe, $^{90}$Y, $^{125}$I, $^{131}$I, $^{186}$Re, and the like. However, besides the mentioned materials above, anything can be used, as long as it can be used in immunological analysis.

To increase the rapidity and competence of analysis, the detecting composition can be immobilized on a suitable carrier or support according to various known methods (Antibodies: A Laboratory Manual, Harlow & Lane; Cold Spring Harbor, 1988). As a example of a suitable carrier or a support, there are agarose, cellulose, nitrocellulose, dextran, sephadex, sepharose, liposome, carboxymethylcellulose, polyacrylamide, polysterine, gabbro, filter paper, ion exchange resin, plastic film, plastic tube, glass, polyamine-methylvinyl-ether-maleic acid copolymer, amino acid copolymer, ethylene-maleic acid copolymer, nylon, cup, flat packs. As other solid substrates, there are cell culture plate, ELISA plate, tube and polymeric membrane. The support may be in a random form, for example, a form of globular (beads), cylindrical (test tube or inside of well), or plane (sheet, test strip).

Preferably, the detecting or diagnosing composition can be in a form of a kit, a microarray, or a protein chip. The diagnosing kit, for example is a lateral flow assay kit using an immune-chromatography for detecting a specific protein in a sample. The lateral flow assay kit includes a sample pad, a releasing pad coated with a detecting antibody, a spreading membrane for developing a sample and performing the antigen-antibody reaction, for example nitrocellulose or strip, and absorption pad.

In an embodiment, there is provided a method of detecting BC200 RNA in a sample, comprising a step of reacting an antibody or its antigen binding fragment with the sample.

The term 'sample' refers to a material which may contains BC200 RNA or is assumed to contain BC200 RNA. The sample can be natural or synthetic material, and obtained by any known method by an ordinarily-skilled person in art. The examples of sample include tissue, cell, whole blood, blood serum, blood plasma, saliva, sputum, lymph fluid, cerebrospinal fluid, intercellular fluid, urine, material for in vitro cell culture such as cell components, cell culture media components or recombinant cell and the like. The determination of the binding to the sample can detect the BC200 RNA in a sample.

In an embodiment, there is provided a composition comprising an antibody or its antigen binding fragment, for diagnosing a disease associated with BC200 RNA selected from the group consisting of a cancer and a neurological disease. For examples, the cancer can be breast cancer, tongue cancer, cervical cancer, esophageal cancer, lung cancer, ovarian cancer and the like. The neurological disease can be Alzheimer's disease.

As disclosed above, BC200 RNA was expressed in various tumorous tissues derived different tissues such as well as nerve tissue, and particularly, BC200 RNA was expressed at a higher degree in metastatic breast cancer rather than benign breast cancer. (Iacoangeli, A., et al., Carcinogenesis. 2004 November; 25(11):2125-33 BC200 RNA in invasive and preinvasive breast cancer.), The expression of BC200 RNA has been reported in breast cancer, cervical cancer, esophageal cancer, lung cancer, ovarian cancer, encephalic cancer and tongue cancer (Chen, W., et al., J Pathol, 1997 November; 183(3):345-51. Expression of neural BC200 RNA in human tumours). The expression of BC200 RNA has been reported in neurological disease such as Alzheimer's disease (Lukiw, W. J., et al., Neurochem Res. 1992 June; 17(6):591-7. BC200 RNA in normal human neocortex, non-Alzheimer dementia (NAD), and senile dementia of the Alzheimer type (AD). 및 Mus, E., P. R. Hof, and H. Tiedge, Proc Natl Acad Sci USA. 2007 Jun. 19; 104(25):10679-84. Dendritic BC200 RNA in aging and in Alzheimer's disease.). Thus, the antibody or its antigen binding fragment of the present invention can be useful for diagnosing for a disease associated with BC200 RNA selected from the group consisting of cancer and a neurological disease, by detecting the expression degree of BC200 RNA in a patient's sample.

As described in KR2011-0075173A, the present inventors reported that the decreased expression amount of BC200 RNA could reduce the cancer metastasis, and proved that BC200 RNA could be a target molecule used for prevention and/or treatment of cancer or cancer metastasis.

An embodiment of the present invention provides a pharmaceutical composition for preventing or treating cancer or cancer metastasis, comprising the antibody or its antigen binding fragment.

In addition, it has been reported in many articles that BC200 RNA was expressed in various cancers and neurological diseases and could be associated with onset, maintenance and progress of the diseases. The antibody or its antigen binding fragment can be used for preventing or treating a disease associated with BC200 RNA selected from the group consisting of cancer and a neurological disease. For examples, the cancer includes breast cancer, tongue cancer, cervical cancer, esophageal cancer, lung cancer, ovarian cancer and the like, and the neurological disease can be Alzheimer's disease.

Besides the antibody or its antigen binding fragment, the pharmaceutical composition can further contain pharmaceutically-acceptable excipients. Herein, the term 'excipient' means a pharmaceutically-acceptable inactive component in a pharmaceutical composition. The suitable excipients for the pharmaceutical composition include 1) diluents such as lactose, mannitol, cellulose, sorbitol and a mixture thereof, 2) slip modifiers such as colloidal silica, talc and a mixture thereof, 3) lubricants such as Magnesium stearate, stearic acid, hydrogenated oil, sodium stearyl fumarate, etc. and a mixture thereof, and 4) colorant or preservative.

The excipients used for the pharmaceutical composition cannot be limited thereto but can include various excipients without limitation.

The pharmaceutical composition in a matrix form can be prepared to the form of tablet and any formulations being suitable for oral administration.

An antibody specific to BC200 RNA or its antigen binding fragment of the present invention can recognize BC200 RNA or regulate the function of BC200 RNA. Accordingly, the antibody can be used for diagnosing and treating a disease associated with BC200 RNA. The detecting method for the RNA-binding antibody according to the present invention can be applied for the preparation of human antibody recognizing a structure of functional RNA.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

FIG. 6 is the CDR sequence of antibody recognizing BC200 RNA and dissociation constant of antibody-RNA complex.

FIG. 10 is the CDR sequence and dissociation constant of antibody-RNA complex of matured clone where the clone derived from MabBC200-A antibody performed the affinity maturation process.

EXAMPLES

Figure 1:
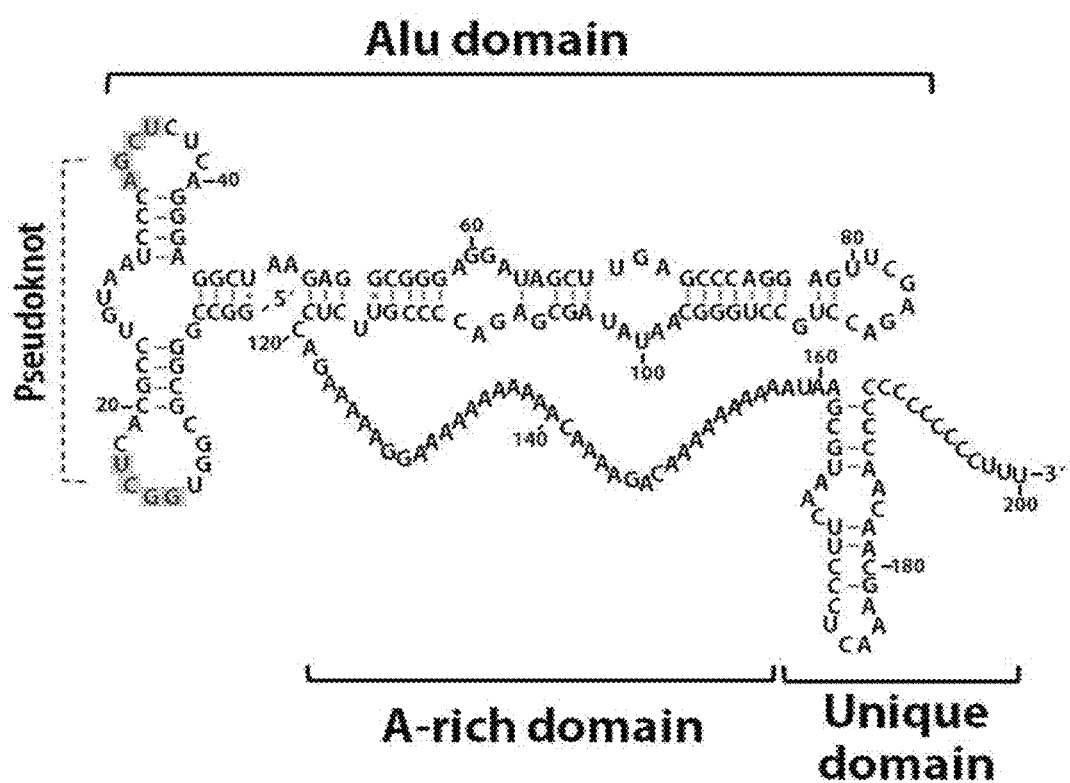
FIG. 1 shows a secondary structure of BC200 RNA

The present invention is further explained in more detail with reference to the following examples. These examples,

Example 1

Preparation of Biotinylated RNA 1.1 BC200 RNA Expression Vector Including an Adaptor RNA To prepare BC200 RNA (SEQ ID NO: 13) including an adapter RNA (SEQ ID NO: 14, ggaucgcauu uggacuucug cccgcaaggg caccacgguc ggaucc) by using in vitro transcription reaction, RNA expression plasmid was constructed. PCR was performed by using a template of human genomic DNA (Roche, Dutch), a forward primer of oligonucleotide (SEQ ID NO: 16, gaattctaat acgactcact ataggccggg cgcggtg) including T7 promoter and a 5-terminal part of BC200, a reverse primer of oligonucleotide (SEQ ID NO: 17, cttccggatc cgaccgtggt gcccttgcgg gcagaagtcc aaatgcgatc caaaggggggg gggggg) including 3'-terminal part of BC200, adapter RNA and StuI region with 2× TOPSimple PreMix-Forte (Enzynomics, Republic of Korea). PCR reaction was performed for 3 minutes at 95° C., for 3 seconds at 95° C., 30 seconds at 55° C. and for 1 minutes at 72° C. in 35 cycles, and then was reacted for 5 minutes at 72° C. in a cycle.

The produced DNA was confirmed by 1.5% agarose gel electrophoresis, and purified with MEGAquick-spin PCR & Agarose Gel DNA Extraction kit (Intron, Republic of Korea). The purified DNA was reacted with T-blunt vector (Solgent, Republic of Korea) and introduced into E. coli DH5α with heat shock treatment. The transformed cell was spread and incubated on solid medium including LB ampicillin (100 μg/ml, ampicillin, Amp) for 16 hours at 37° C. and then, the single colony was inoculated in 3 ml of liquid medium including LB ampicillin 100 μg/ml) and incubated for 16 hours at 37° C. DNA was extracted from the culture solution by using DNA-spin Plasmid DNA Purification kit (Intron, Republic of Korea) and the nucleotide sequence was analyzed (Solgen, Republic of Korea). The result confirmed that the extracted DNA was the same as T7 promoter, BC200 RNA, adapter RNA, and StuI region.

1.2 RNA Preparation Using In Vitro Transcription

The DNA obtained in Example 1.1 was cut with restriction enzyme StuI, the cleavage fragments were confirmed by 1.5% agarose gel electrophoresis, and then purified with MEGAquick-spin PCR & Agarose Gel DNA Extraction kit. The purified DNA was reacted with RiboMAX™ Large Scale RNA Production Systems for T7 kit (Promega, USA), separated by using 5% PAGE including 7M urea to obtain RNA band, and was eluted with RNA elution solution (Tris-Cl, pH7.5, 0.3M NaCl, 1 mM EDTA, 0.1% SDS) for 16 hours at 4° C.

The eluted solution was centrifuged at 15,000×g for 1 hour and the supernatant was filtrated with a filter having a pore size of 0.4 μm. The product was centrifuged with addition of the same amount of phenol at 15,000×g for 10 minutes, and then the supernatant was transferred to a tube. The same amount of chloroform was added to the tube and centrifuged at 15,000×g for 10 minutes. The supernatant was transferred to a new tube and was added by 2.5 times amount of ethanol as the amount of supernatant and then stored at −70° C. The stored solution was centrifuged at 2 to 8° C., 15,000×g, for 5 minutes to remove ethanol, centrifuged with the sequential addition of 70% aqueous ethanol and 100% ethanol, and the supernatant was removed. The produced RNA pellet was dried for 3 minutes at a room temperature with a vacuum pump.

1.3 RNA Biotinylation

The RNA obtained in Example 1.2 was mixed at ratio of 1:2.5 with a biotinylated oligonucleotide (SEQ ID NO: 15, aggatccgac cgtggtgccc t) being capable of binding complimentarily to the RNA and the adapter RNA, reacted at 85° C. for 5 minutes, and then was cooled slowly to a room temperature to obtain biotinylated RNA.

Example 2

Change of Human Antibody Library in Fab Form (Antigen Binding Fragment) into Phage Display Library The library cells including a kappa light chain and a lambda light chain as Fab form of large human antibody library at 6:4 which corresponded to the same ratio of human organism were inoculated at $1.5 \times 10^{11}$ cells on a medium (2.1 L) including 2YT and ampicillin 100 μg/ml, incubated for 2 to 3 hours at 37° C. ($OD_{600}$=0.7~0.8), and infected with the helper phage of VCSM13 to be 1:20 of MOI value. The infected cells were cultured in a static culture at 37° C. for 30 minutes and then at 37° C. for 30 minutes in a shaking culture. Then, the culture solution was added by kanamycin (70 μg/ml, Kan) and cultured at 30° C. for 16 hours.

The cultured cells was centrifuged at 4° C., 5,000 rpm for 15 minutes (Supra 22K, A500s-6 No. 11, HANIL SCIENCE INDUSTRIAL, Republic of Korea), and the supernatant was reacted on ice with addition of 5 mM PEG (polyethylene glycol) 8000 and 500 mM NaCl. The product was centrifuged at 4° C., 10,000 rpm for 1 hour (Supra 22K, A500s-8 Rotor No. 7, HANIL SCIENCE INDUSTRIAL, Republic of Korea) and the supernatant was removed completely to obtain RNA pellet. The produced pellet was dissolved in 10 ml PBS and centrifuged at 13,000×g, for 10 minutes. Then, the obtained solution including a phage library was transferred to a new tube and stored at −70° C.

Example 3

Panning Process of RNA 3.1 Streptavidin Coating

Immunotube was coated at 4° C., for 16 hours with 100 g of streptavidin dissolved in 1 ml of coating buffer solution (15 mM $Na_2CO_3$, 34.84 mM $NaHCO_3$, pH 9.6) and washed once with 0.05% PBST (PBS containing 0.05% of Tween20). The product was reacted for blocking the reaction with addition of 2 ml of 3% BSA at a room temperature for 1 hour and washed twice with 0.05% PBST.

3.2 Removal of Negative Antibody Reacting with the Biotinylated Oligonucleotide and Streptavidin 1 ml ($1.2 \times 10^{13}$/ml) of the phage-displayed library antibody of Example 2 and 100 pmol of biotinylated oligonucleotide were added to the immunotube obtained in Example 3.1, and incubated at a room temperature for 30 minutes. Then, the phage unbound with the antibody (negative control) was added to the immunotube obtained in Example 3.1 and incubated at a room temperature for 30 minutes, which was repeated two times, to remove the phage binding to the negative control.

3.3 Selection of Antibody Binding to RNA

After removing the phage bound to the negative control in Example 3.2, the library phage antibody was reacted for 1 hour with 10 pmol of the biotinylated RNA of Example 1.3, and was added to the immunotube of Example 3.1 and reacted at a room temperature for 30 minutes.

3.4 Removal of Antibody with a Weak Binding Affinity to RNA

The immunotube of Example 3.3 was washed with 0.05% PBST at ten times. As the number of panning round was larger, the number of washing increased by 10 times. For examples, the washing step was performed at twenty times for secondary panning, at thirty times for third panning, and at forty times for fourth panning.

3.5 Elution of Phage Bound to RNA 5 mg of yeast total RNA (life technology) dissolved in 1 ml of PBS was added to the immunotube of Example 3.4 and reacted at a room temperature for 10 minutes to separate only antibody bound to RNA.

3.6 Change of Panning Product into Colony, Storage of Colony and Change to the Phage-Displayed Colony to be Used for the Next Step.

Single colony of E. coli TG1(F' [traD36 proAB$^+$ lacI$^q$ lacZΔM15]supE thi-1 Δ(lac-proAB) Δ(mcrB-hsdSM)5, (rK$^-$mK$^-$)) was culture in 2YT medium (10 ml) at 37° C. for 2 to 3 hours to produce a culture solution (OD$_{600}$=0.7~0.8). The culture solution was infected with the eluted phage obtained in Example 3.5, left at 37° C. for 30 minutes and cultured at 37° C. for 30 minutes in a shaking culture. The culture solution was centrifuged at 4° C., 3,500 rpm for 10 minutes (Supra 22K, Rotor A500s-8 No. 7, HANIL SCIENCE INDUSTRIAL, Republic of Korea), and the supernatant was removed to obtain RNA pellet. The pellet dissolved in 1 ml of 2YT medium was spread and cultured at 37° C. for 16 hours on a solid medium including SOB, 10 mM MgCl$_2$, 100 mM glucose and 100 μg/ml of ampicillin. The cultured colony was dissolved in 10 mL of medium including 2YT, 100 mM Glucose, 5 mM MgCl$_2$ and 100 μg/ml of ampicillin and transferred to a new tube and stored at −70° C.

To change the stored colony into a phage-displayed type, the cells were melt and added to the medium including 2YT and 100 μg/ml of ampicillin to reach OD$_{600}$=0.1~0.15. after culturing the cells at 37° C. for 2 to 3 hours (OD600=0.7~0.8), the helper phage VCSM13 was added to achieve 1:20 of MOI value product and was cultured at a static culture at 37° C. for 30 minute and at a at 37° C. for 30 minute by shaking. The produced culture was added by 70 μg/ml of kanamycin (Kan) and cultured at 30° C. for 16 hours. The cultured cells were centrifuged at 4° C. and 5,000 rpm for 15 minutes (Supra 22K, A500s-6 Rotor No. 11, HANIL SCIENCE INDUSTRIAL, Republic of Korea), and the supernatant was reacted on ice with addition of 5 mM PEG (polyethylene glycol) 8000 and 500 mM NaCl. The product was centrifuged at 4° C., 10,000 rpm for 1 hour (Supra 22K, A500s-8 Rotor No. 7, HANIL SCIENCE INDUSTRIAL, Republic of Korea) and the supernatant was removed completely to obtain RNA pellet. The produced pellet was dissolved in 10 ml PBS and centrifuged at 13,000×g, for 10 minutes. Then, the obtained solution including a phage library was transferred to a new tube and stored at −70° C.

The processes of Examples 3.1 to 3.6 were repeated four times and the results are shown in Table 1.

TABLE 1

| Number of panning round | Number of initial phage | Number of bound phage |
|---|---|---|
| 1 | 1.2 × 10$^{13}$ | 6.1 × 10$^6$ |
| 2 | 3.0 × 10$^{13}$ | 9.9 × 10$^6$ |
| 3 | 1.8 × 10$^{13}$ | 9.7 × 10$^7$ |
| 4 | 1.2 × 10$^{13}$ | 2.2 × 10$^8$ |

Example 4

The Confirmation of Panning Results Using RNA ELISA and Dot-Blot Analysis 4.1 The Confirmation of Panning Results Using RNA ELISA The cell stocks performed by panning at first round to fourth round and frozen in Example 3 were changed into the phage form according to the same method of Example 3.6. 96-well ELISA plate (#439454, NUNC, Denmark) was coated with each 100 ng of streptavidin per well at 4° C. for 16 hours, and then was washed once with 0.05% PBST 200 μl and blocked with 3% BSA dissolved in 0.05% PBST. At the same time, 100 μl phage-displayed antibody binding to BC200 RNA after performing first to fourth panning rounds was reacted with 4 pmol of biotinylated BC200 RNA at a room temperature. Each blocked well was washed twice with 0.05% PBST 200 μl and reacted for 1 hour with the addition of the phage-displayed antibody and the biotinylated BC200 RNA. Each well was washed at three times with 0.05% PBST 200 μl and then was reacted at a room temperature for 1 hour with a diluted secondary antibody of anti-human IgGF(ab)$_2$'-HRP (Pierce, USA) at a dilution ratio of 1:2000.

The wells were washed at four times with 200 μl of 0.05% PBST containing PBS-Tween 20 (0.05%) and were colored for 5 minutes with the addition of substrate solution of BD OptEIA TMB Substrate Reagent Set (BD, USA) at an amount of 100 μl per each well, and the reaction was terminated with 50 μl of 2.5M sulfuric acid solution. The absorbance of reaction product was detected with spectrophotometer (Molecular Device, USA) at 450 nm to show the result in FIG. 2.

Figure 2:
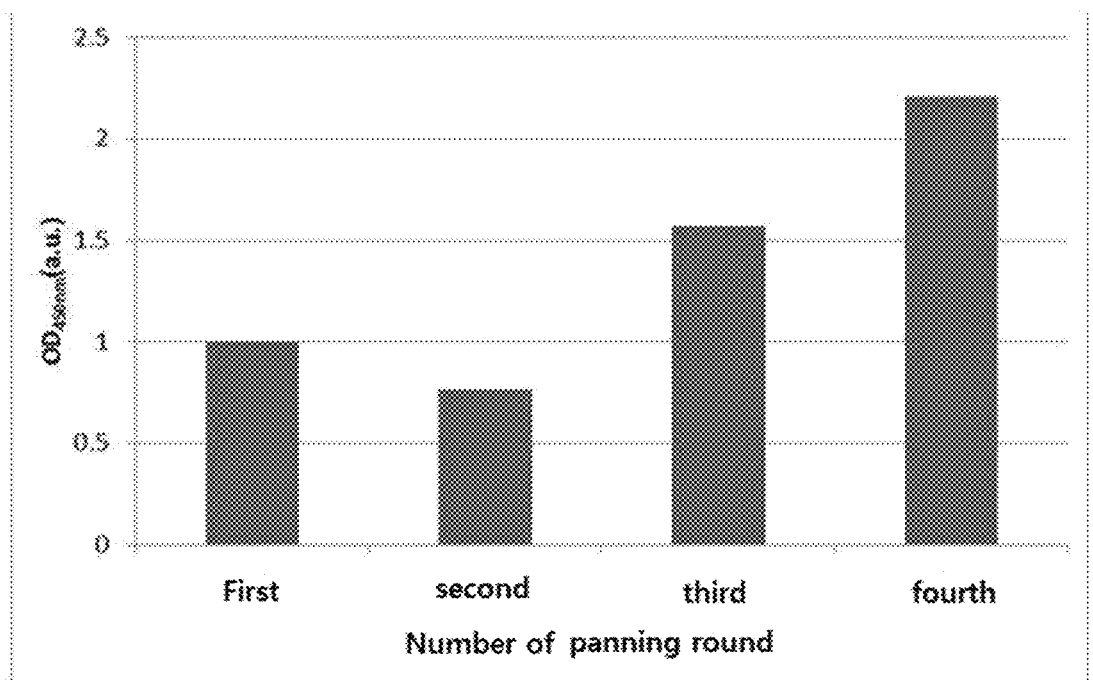
FIG. 2 is an ELISA result showing the binding affinity of polyclonal Fab antibody displayed on a phage selected by the panning method.

As shown in FIG. 2, the antibody tilter increased from the third panning round of BC200 RNA.

4.2 the Confirmation of Panning Results Using Dot-Blot Analysis

The cell stocks obtained from the fourth panning round according to Example 3 were melt and spread on the medium including 2YT and 100 μg/ml of ampicillin to differentiate a single colony and then was cultured at 37° C. for 16 hours. To convert the monoclonal antibody into phage-displayed type again, the cell stocks were melt and inoculated on the medium including 2YT and 100 μg/ml of ampicillin to obtain the phage type according to the same method of Example 3.6. The control is a monoclonal antibody prepared and separated randomly from human antibody library. 100 μl of the antibody-displaying phages were added to Dot-blot kit (schleicher and schuell, Dutch) and bound to Hybond-ECL membrane (GE, USA) at a room temperature for 1 hour. The membrane was blocked with 2% skim milk dissolved in PBS at a room temperature for 1 hour, and was cross-linked at 85° C. oven for 1 hour. The cross-linked membrane was incubated for 16 hours at rotator with Rapid-hyb buffer (GE, USA) including BC200 RNA labeled with α-$^{32}$p[CTP] as a probe. At that time, the used BC200 RNA was obtained by reacting at 65° C. for 5 minute to form the secondary structure and further reacting at 4° C. for 10 minutes. Finally, the membrane was washed with washing solution I (2×SSC, 0.1% SDS) and washing solution II (0.2×SSC and 0.1% SDS) and was exposed to the light with imaging plate (Fujifilm, Japan). The obtain signal was detected with BAS7000 (Fujifilm, Japan) and shown in FIG. 3.

Figure 3:
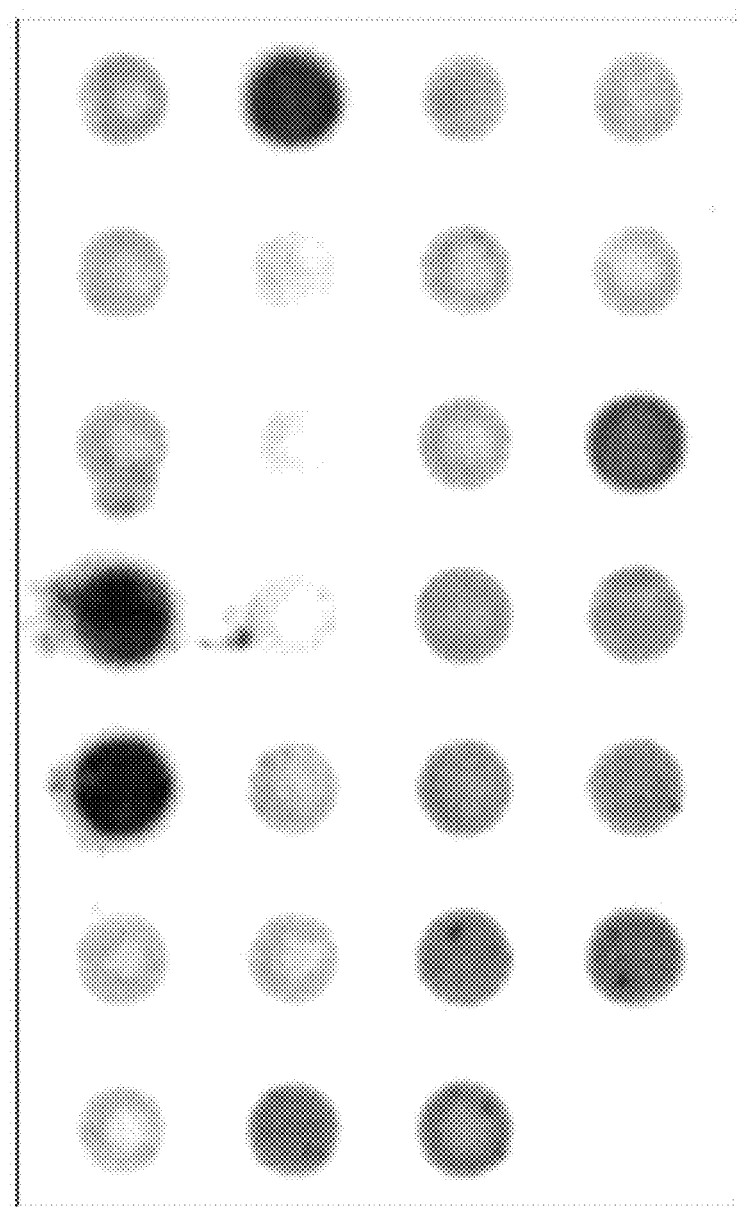
FIG. 3 is a dot-blotting analysis result showing the binding affinity of monoclonal Fab antibody displayed on a phage selected by the panning method.

As represented in FIG. 3, the monoclonal antibodies with a strong binding affinity to BC200 antigen were detected and named as MabBC200-A and MabBC200-B.

Example 5

Whole IgG Expression Vector of Animal Cell 5.1 Analysis of Whole IgG1 Transformation To transform Fab form of human monoclonal antibody binding to BC200 RNA into whole IgG1 antibody, 1 fmol of monoclonal DNA, 15 pmole of each forward primer and reverse primer for amplifying a heavy chain or a light chain (SEQ ID NO: 20 to SEQ ID NO: 31) and 2× TOPSimple PreMix-Forte (Enzynomics, Republic of Korea) were mixed and reacted according to SOEing PCR method. The synthesized DNA was performed by 1.5% agarose gel electrophoresis and the DNA band with expected size was cut and purified with MEGAquick-spin PCR & Agarose Gel DNA Extraction kit (Intron, Republic of Korea). The purified DNA was cut with a restriction enzyme and ligated to pdCMV-dhfrC-chimeric vector (Eung Suk, L., et al., Exp. And Mol. Med., 2012) by mixing with 1 μl (10 ng) of pdCMV-dhfrC-chimeric vector, 15 μl of heavy chain (100~200 ng), 2 μl of 10× buffer solution, 1 U of ligage (Promega, USA) and distilled water, and keeping the mixture at 17° C. for 16 hours. The produced vector was introduced into E. coli DH5α with heat shock treatment. The transformed cells were spread on the solid medium of LB ampicillin (100 μg/ml, ampicillin, Amp) and incubated at 37° C. for 16 hours. Then, the single colony was inoculated in 3 ml of liquid medium including LB ampicillin 100 μg/ml) and cultured for 16 hours at 37° C. DNA was extracted from the culture solution by using DNA-spin Plasmid DNA Purification kit (Intron, Republic of Korea) and the sequence was analyzed (Solgen, Republic of Korea). As a result, the sequences of heavy chain and light chain of BC200 RNA-binding antibody in whole IgG1 type were the same as those of Fab type.

5.2 Investigation of Whole IgG

36 μl of Noble enhancer, 40 μl of Noble factor (Noble Bioscience, Republic of Korea) and 10 μg of whole antibody DNA were transformed into 293T cell. The supernatant of transformed 293T cell was purified with the recombinant protein G agarose (Invitrogen, USA) and the eluted solution was confirmed by using SDS-PAGE and ELISA. The results were shown in FIG. 4 and FIG. 5.

Figure 4:
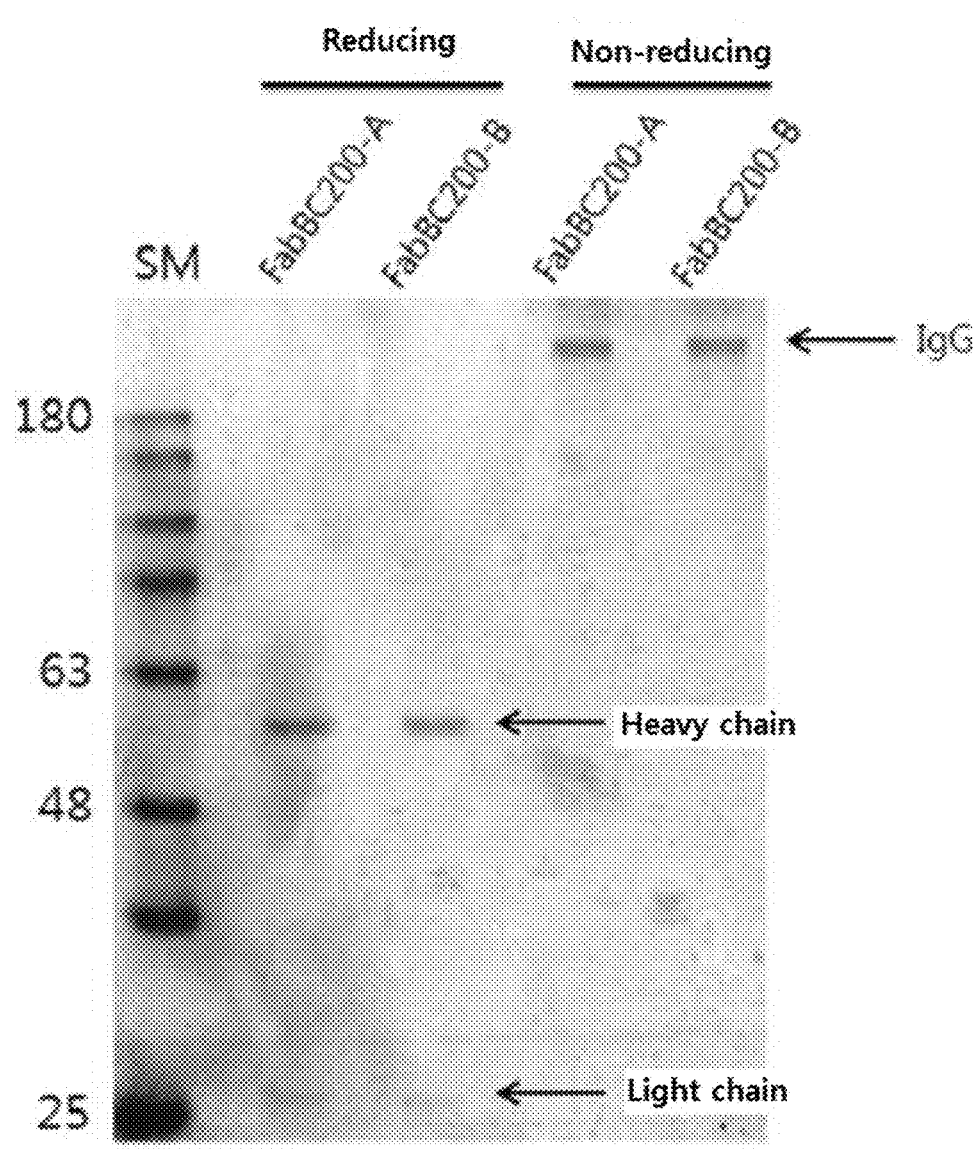
FIG. 4 is a SDS-PAGE result of the antibody obtained by expressing and purifying it in an animal cell line.
Figure 5:
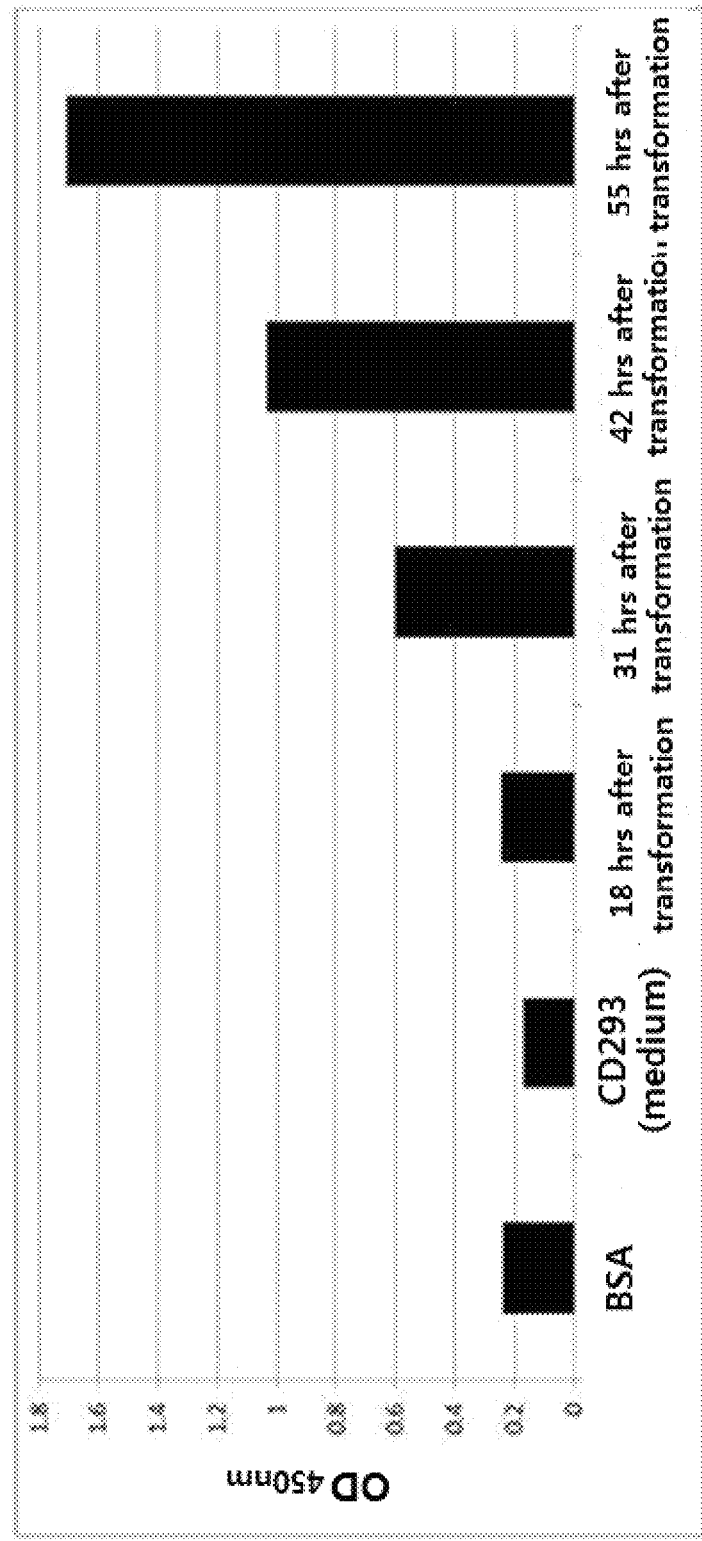
FIG. 5 is an ELISA result of the antibody obtained by expressing and purifying it in an animal cell line.

As shown in FIG. 4 and FIG. 5, whole IgG1 form was successfully converted from Fab from.

Example 6

Test for the Binding Affinity of Whole IgG1 Monoclonal Antibody 6.1 Binding Affinity of Monoclonal Antibody Using the Filter Binding Assay Various concentrations of the monoclonal antibody of Example 5 were obtained by diluting the antibody, were reacted at 65° C. for five minutes and at 4° C. for 10 minutes, and then was reacted with the same amount of BC200 RNA at a room temperature for 30 minutes. At that time, an antibody control was an antibody produced by using pdCMV-dhfrC-chimeric-A10A3 vector (Eung Suk, L., et al., Exp. And Mol. Med., 2012) and the 6S RNA derived from E. coli was used as RNA control.

The product was added to Dot blot kit (schleicher and schuell, Dutch) and passed to Hybond-ECL membrane (GE, USA) and Hybond-XL (GE, USA) in sequential manner. To analyze the amount of unbound BC200 RNA, the test using only BC200 RNA without antibody was performed at the same time. The Hybond-XL membrane was cross-linked at 85° C. oven for 1 hour and reacted for 16 hours with the Rapid-hyb buffer (GE, USA) BC200 RNA labelled with α-$^{32}$p[CTP] as a probe.

Finally, the membrane was washed with washing solution I (2×SSC, 0.1% SDS) and washing solution II (0.2×SSC 0.1% SDS) and exposed to the light with imaging plate (Fujifilm, Japan). The obtain signal was detected with BAS7000 (Fujifilm, Japan).

6.2 Binding Affinity of Monoclonal Antibody in Whole IgG Form to BC200 RNA

The dissociation constant of was calculated from the result of Example 5.2 according to following mathematical formula 1 and the result was represented in FIG. 2.

$$[RNA - Ab] \leftrightarrows [RNA] + [Ab]$$ [Mathematical Formula 1]

$$Kd = [RNA][Ab]/[RNA - Ab]$$

Figure 7:
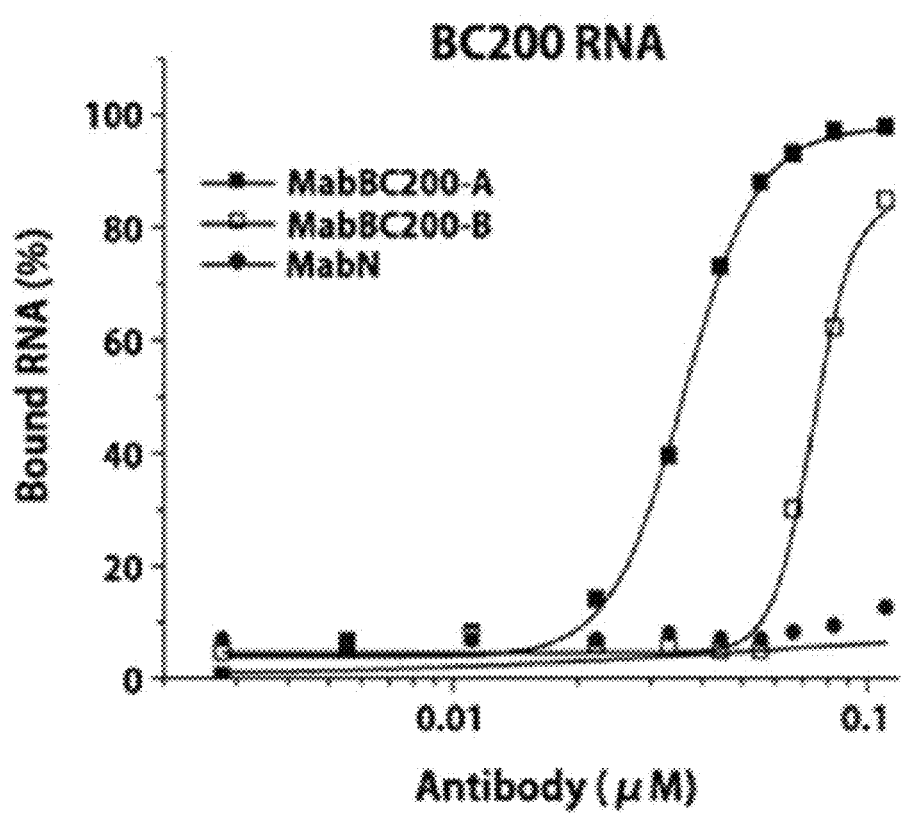
FIG. 7 shows the binding method for obtaining the dissociation constant of antibody-RNA complex.
Figure 8:
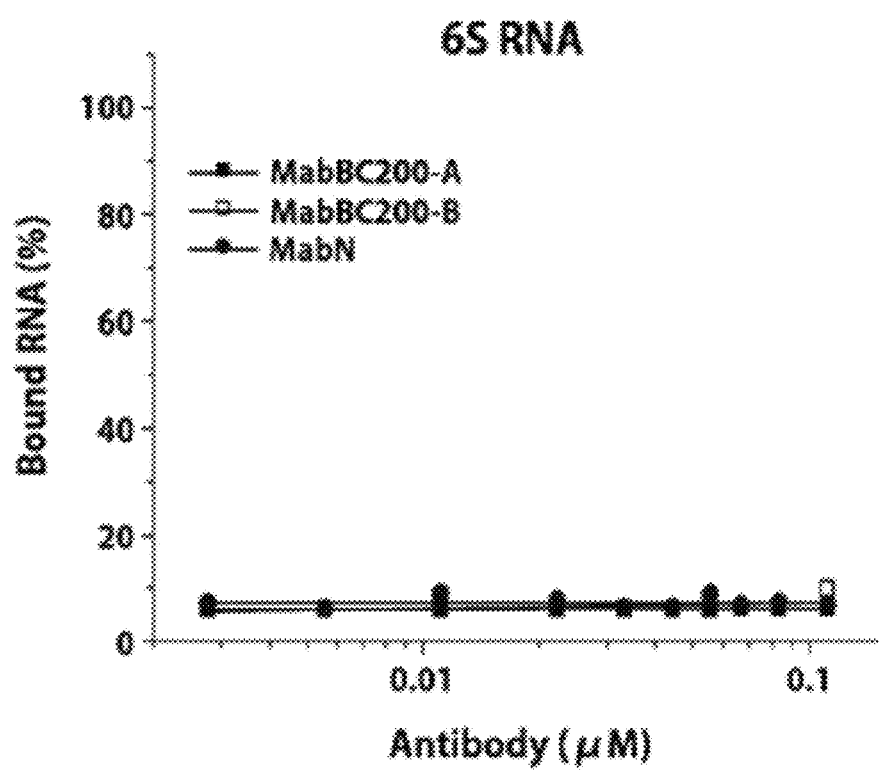
FIG. 8 shows the binding method for obtaining the dissociation constant using 6S RNA derived from E. coli as a negative control.

$\ominus$ = Ratio of $RNA$ bound to the antibody, $\ominus$ = $RNA$ bound to the antibody/total $RNA$ = $[RNA - Ab]/\{[RNA] + [RNA - Ab]\}$ = $[Ab]/(Kd + [Ab])$ As represented in Table 2, the dissociation constants, Kd of MabBC200-A and MabBC200-B were 3.6×10$^{-8}$ M and 7.6×10$^{-8}$ M, respectively (FIG. 6 to FIG. 8).

TABLE 2

| | MabBC200-A | MabBC200-B |
|---|---|---|
| Dissociation constant (K$_d$) (M) | 3.6 × 10$^{-8}$ | 7.6 × 10$^{-8}$ |

Because the library was derived from human naïve antibody and has not any specific property, the presence of six common amino acids showed that the amino acids would played an important role in the interaction with BC200 RNA.

Example 7

Affinity Maturation

Figure 9:
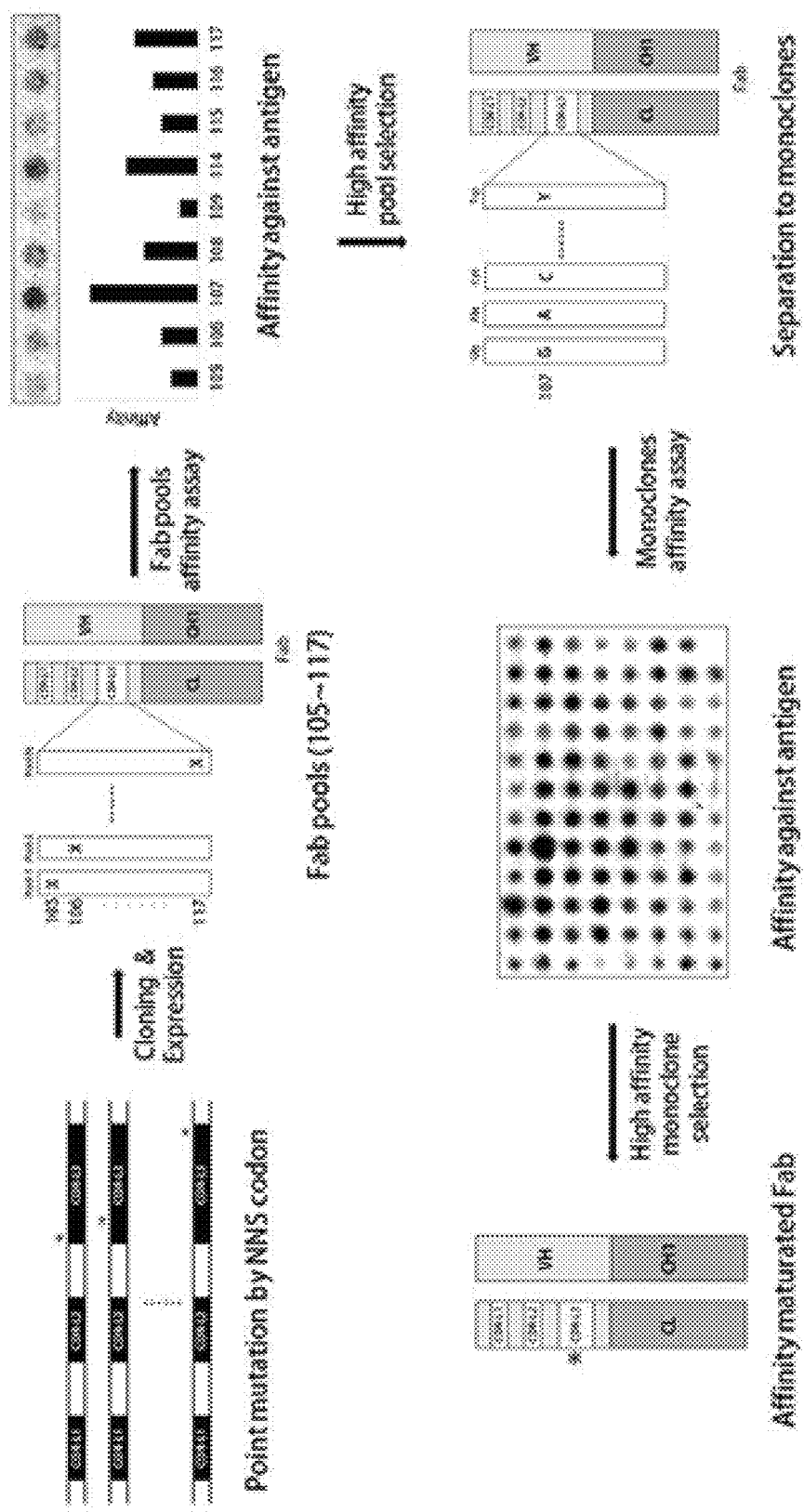
FIG. 9 is a schematic drawing for new affinity maturation using the sib selection method accompanied by PCR mutation method.

The affinity maturation was performed by using MabBC200-A having a high affinity, in order to increase an affinity of binding to BC200 RNA (FIG. 9). Unlike the conventional method, the sib selection and PCR mutation method using random codon were used for increasing the binding affinity to RNA. The affinity maturation process was shown in FIG. 5. The key principle was sib selection accompanying by PCR mutation using the primer including NNS codon (N=A, G, C, T; S=G, C). The sib selection means a screening method performed into two steps of an upstream screening and a downstream screening. More specifically, at least an amino acid was randomly introduced into each nine positions in CDR3 of light chain in the present invention to produce nine pools, and the binding affinity of nine pools to BC200 RNA were tested to perform the upstream screening.

96 clones to cover all twenty amino acids at 90% or higher were analyzed and shown in following formula.

$$P = \frac{1}{X^N} \times (X^N - (xCx-1 \times (x-1)^N - xCx-2 \times (x-2)^N + - + - ...))$$

Wherein, P is a possibility of covering all clones,
X is the number of clones to be covered, and
N is the number of clones to be tested.

Then, the downstream screening was performed to confirm the clone having the highest binding affinity among 96 clones.

Figure 11:
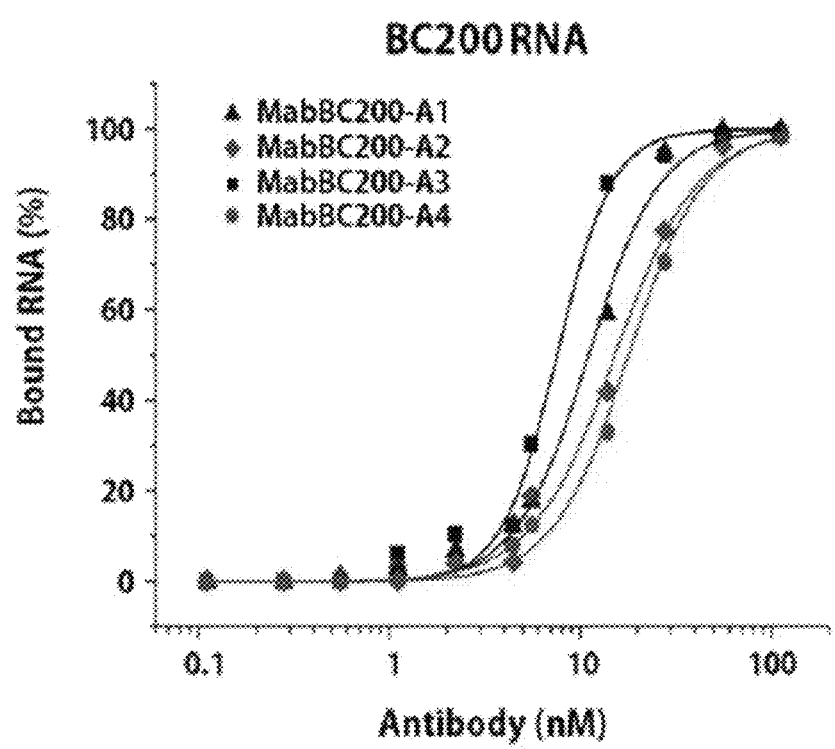
FIG. 11 shows the binding method for obtaining the dissociation constant of antibody-BC200 RNA where the antibody performed the affinity maturation process.

The analysis confirmed that four clones derived from MabBC200-A have higher binding affinity than the known clone, and were named as MabBC200-A1, MabBC200-A2, MabBC200-A3, and MabBC200-A4. As a result of analyzing the binding affinity of each clone, Kds were 2 to 5 times higher than conventional MacBC200-A (FIG. 10 and FIG. 11). Particularly, MabBC200-A3 had the highest affinity.

Example 8

Sequence Analysis of Mab Antibody

The clones of monoclonal antibodies binding specifically to BC200 RNA which was confirmed in Example 6 were incubated in 2YT and ampicillin (100 µg/ml) at 37° C. for 16 hours. DNA was extracted from the cultured single clone by using DNA-spin Plasmid DNA Purification kit (Intron, Republic of Korea). The nucleotide sequences of heavy chain and light chain were analyzed using primer H(SEQ ID NO: 18, gcgaagtcac ccatcagg) and primer L (SEQ ID NO: 19, tagctcactc attaggca) with ABI-3730xl automatic sequencer (Solgent, Republic of Korea), to show the result in Table 3. In four clones of MabBC200-A1, MabBC200-A2, MabBC200-A3, and MabBC200-A4 derived from MabBC200-A, CDR3 nucleotide sequences of each variable region of light chain were mutated clones of S107G, S107A, S107C, and S107V. Table 3 represents the amino acid sequence of CDR3 in the antibody binding to Mab BC200 RNA.

Example 9

Investigation of a Binding Region of BC200 RNA to the Antibody

To investigate the part of BC200 RNA binding to the antibody, the RNA footprinting was carried out by using hydroxyl radical and $Pb^{2+}$. MabBC200-A3 having the highest binding activity in Example 6 was used. The hydroxyl radical footprinting was performed by Fenton reaction using Iron/EDTA. 3'-terminus of BC200 RNA was labeled with [$^{32}$P]pCp by using T4 RNA ligase, heated at 65° C. for 5 minutes, and cooled on ice for 10 minutes and maintained at a room temperature. Then, 1 µl of 5 mg/ml heparin was reacted with 1 µg of yeast total RNA and its corresponding antibody to be final volume of 7 µl. The reaction was carried out in PBS at room temperature for 30 minutes. 1 µl of 1 mM $Fe(II)(NH_4)_2(SO_4)_2$, 1 µl of 1.25 mM EDTA, and 1 µl of 60 mM Sodium ascorbate were added and reacted at a room temperature for 30 minutes, and stopped with 1 µl of 100 mM thiourea and 11 µl of gel loading buffer II (Ambion). The obtain sample was boiled at 95° C. for 5 minutes and loaded on sequence gel of 5% (v/v) polyacrylamide and 9M urea. The RNase T1 ladder (Ambion, USA) was prepared according to the manufacturer's manual.

The test of RNA footprinting method found that a domain region of $60^{th}$ to $110^{th}$ nucleotide of BC200 RNA (SEQ ID NO: 13) was used for the antibody binding. To investigate how the region binds to the antibody, RNA fragment consisting of 73 nucleotides was prepared.

Figure 12:
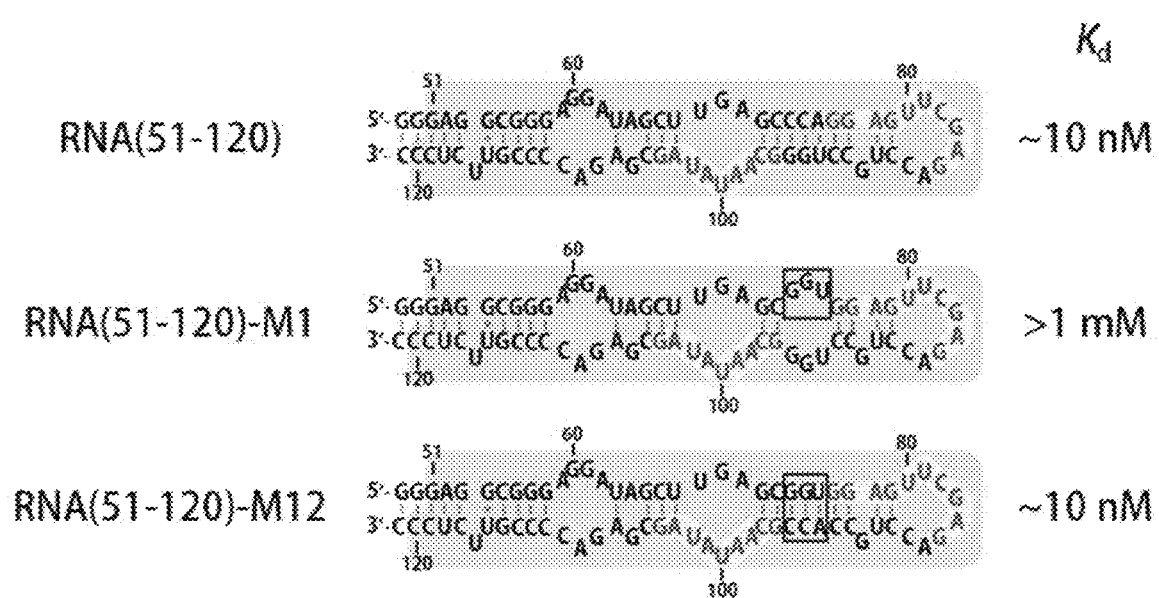
FIG. 12 shows the secondary structures of RNA (51-120) and its derivatives, where RNA (51-120) consists of 73 nucleotides including a nucleotide sequence of 51th nucleotide to $120^{th}$ nucleotide of BC200 RNA, two additional nucleotides at 5'-end and an additional nucleotide at 3'-end and the binding site of MabBC200-A3 is marked.

The prepared RNA contains RNA (51-120) including 51th to $120^{th}$ nucleotides of BC200 RNA, and further 2 nucleotides at 5'-terminus (GG) and 1 nucleotide at 3'-terminus (C). The result of filter binding method confirmed that RNA had about 10 nM of dissociation constant (Kd) and that RNA also bound to the antibody (FIG. 12). To investigate that the nucleotide sequence of BC200 RNA plays an important role in binding to the antibody, single strand of 11 nucleotides was selected among 19 nucleotides of binding region and the library having a random nucleotide inserted into the single strand consisting of 11 nucleotides was prepared.

Figure 13:
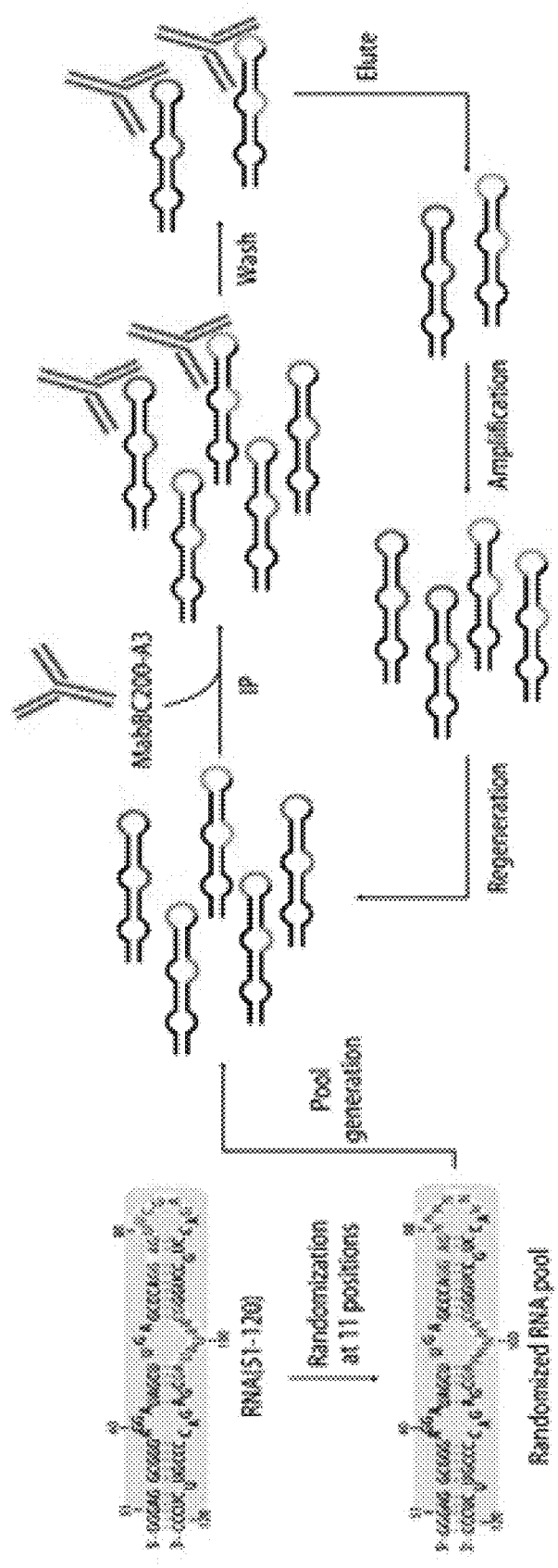
FIG. 13 is a schematic SELEX drawing for detecting the RNA binding site being in antibody MabBC200-A3 (IP: precipitation).

The library obtained from RNA (51-120) had a variety of $4^{11}$ ($4.2 \times 10^6$) and was used for SELEX (systematic evolution of ligands by exponential enrichment) (FIG. 13). To remove the false positive binders, at the initial round, RNA 0.2 ng ($4.2 \times 10^6$ molecules) was reacted with 10 µl of protein G agarose (Invitrogen, USA) for 30 minutes in PBS 50 µl,

TABLE 3

| Antibody | Chain | CDR1 | CDR2 | CDR3 |
|---|---|---|---|---|
| MabBC200-A | variable region of heavy chain | GYTLSAYY (SEQ ID NO: 1) | INPRGGRT (SEQ ID NO: 2) | CAARGSPRSRFYY GMGVW (SEQ ID NO: 3) |
| | variable region of light chain | QSINNY (SEQ ID NO: 4) | ATS (SEQ ID NO: 5) | CQQSYSFPWTF (SEQ ID NO: 6) |
| MabBC200-A1 | variable region of light chain | QSINNY (SEQ ID NO: 4) | QSINNY (SEQ ID NO: 4) | CQQGYSFPWTF (SEQ ID NO: 7) |
| MabBC200-A2 | variable region of light chain | QSINNY (SEQ ID NO: 4) | QSINNY (SEQ ID NO: 4) | CQQAYSFPWTF (SEQ ID NO: 8) |
| MabBC200-A3 | variable region of light chain | QSINNY (SEQ ID NO: 4) | QSINNY (SEQ ID NO: 4) | CQQCYSFPWTF (SEQ ID NO: 9) |
| MabBC200-A4 | variable region of light chain | QSINNY (SEQ ID NO: 4) | QSINNY (SEQ ID NO: 4) | CQQVYSFPWTF (SEQ ID NO: 10) | and with 2.8 nM MabBC200-A3 in PBS 100 μl at room temperature for 30 minutes. The produced antibody-RNA complex was immune-precipitated by using protein G agarose and the precipitate was washed with PBS containing 0.05% Tween-20, and RNA extracted with phenol. The RNA was recovered with ethanol precipitation method and was amplified by RT-PCR.

The primers for performing the RT-PCR reaction are shown as follows:

RNA (51-120)-T7-up (SEQ ID NO: 32):

5'-CCGGAATTCTAATACGACTCACTATAGGGAGGCGGGAGGATAGC-3'

RNA (51-120)-T7-dn (SEQ ID NO: 33):

5'-TCC CCCGGGAGAACGGGGTCTCGC-3'

The amplified cDNA was used for preparing RNA used in next round RNA. After 8 rounds, the amplified cDNA was cloned into T-blunt vector (Solgent, Republic of Korea) and its sequence was analyzed to represent the result in Table 4 (Table 4).

TABLE 4

| RNA | Frequency | Sequence (5'→3') |
|---|---|---|
| RNA (51-120) | — | GGGAGGCGGGAGGAUAGCUUGAGCCCAGGAGUUCGAG ACCUGCCUGGGGCAAUAUAGCGAGACCCCGUUCUCCC |
| Randomized RNA pool | — | GGGAGGCGGGAGGAUAGCUUGAGCCCAGGAGNNNNNN ACCUGCCUGGGGCNNNNNAGCGAGACCCCGUUCUCCC |
| S1 | 46 | GGGAGGCGGGAGGAUAGCUUGAGCCCAGGAGUUCGAG ACCUGCCUGGGGCAAUAUAGCGAGACCCCGUUCUCCC |
| S7 | 1 | GGGAGGCGGGAGGAUAGCUUGAGCCCAGGAGCAAGCG ACCUGCCUGGGGCAGUAUAGCGAGACCCCGUUCUCCC |
| S14 | 1 | GGGAGGCGGGAGGAUAGCUUGAGCCCAGGAGUAUUCU ACCUGCCUGGGGUAUCCAGCGAGACCCCGUUCUCCC |
| S40 | 1 | GGGAGGCGGGAGGAUAGCUUGAGCCCAGGAGUAUCGC ACCUGCCUGGGGCUAUAUAGCGAGACCCCGUUCUCCC |
| S50 | 1 | GGGAGGCGGGAGGAUAGCUUGAGCCCAGGAGACACUU ACCUGCCUGGGGCUAAGCAGCGAGACCCCGUUCUCCC |

The bold characters in Table 4 refer to the binding region of antibody MabBC200-A3, the randomized sequence was shown in box, and BC200 RNA and other sequences are marked with shading.

Figure 14:
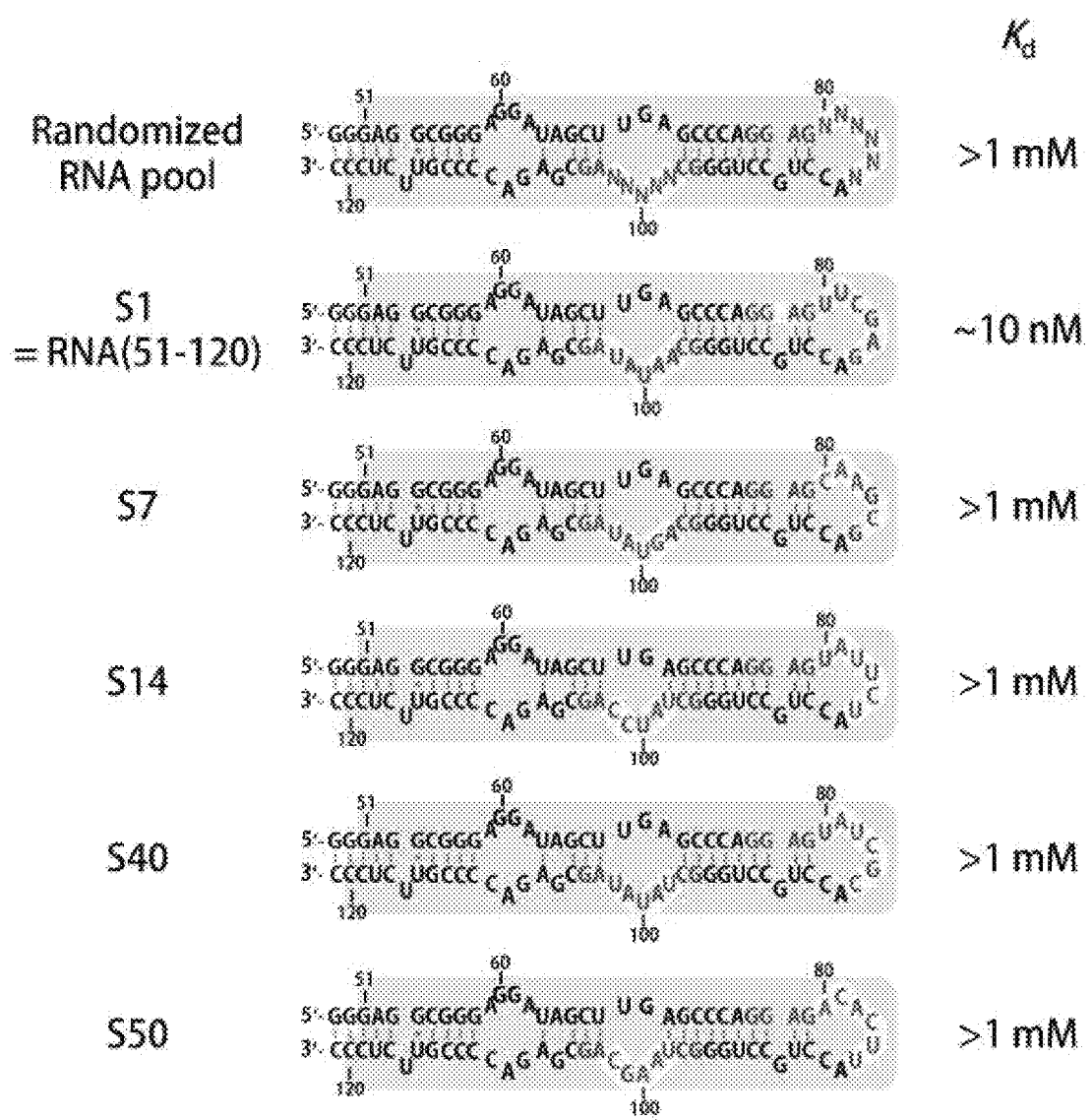
FIG. 14 is a secondary structure of RNA selected after performing eight rounds of SELEX, where the antibody-binding site is marked in red and the randomized sequences are marked with box.
Figure 15:
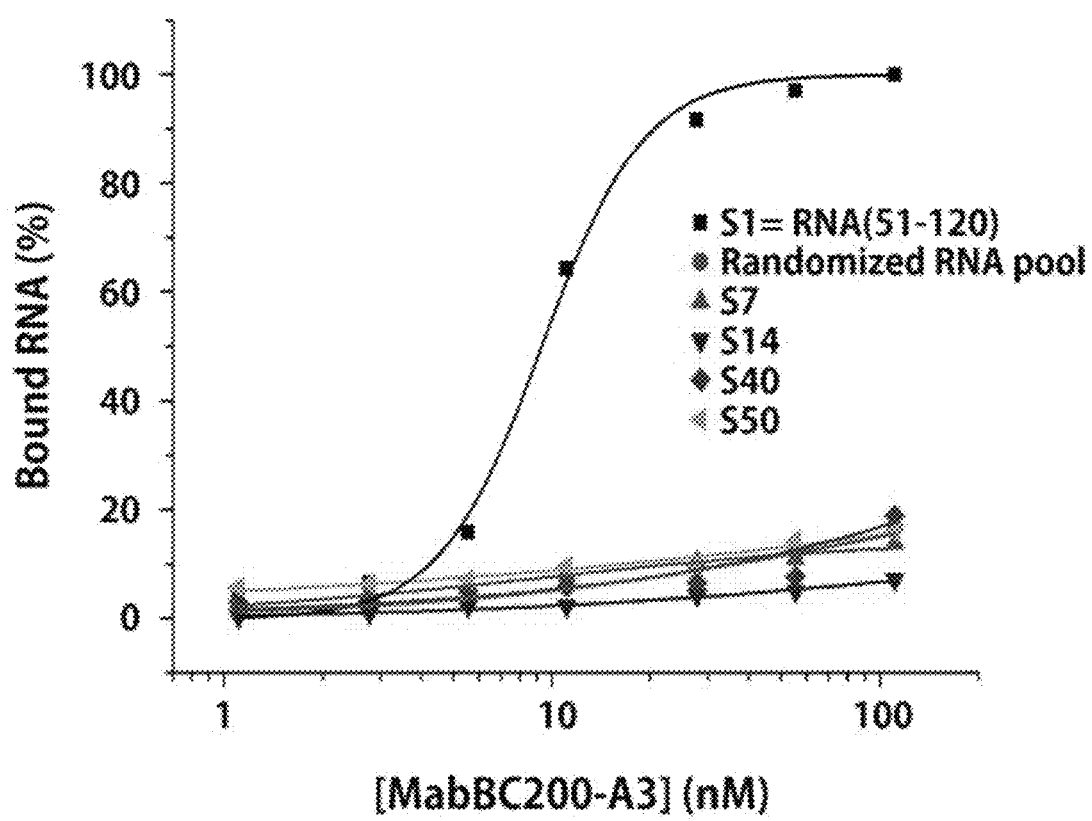
FIG. 15 shows the binding method for obtaining the dissociation constant of each RNA-antibody complex.

After 8$^{th}$ round selection, 50 single clones are selected. Surprisingly, 46 clones have the same nucleotide sequences as RNA (51-120). Unlike 46 clones, 4 clones includes 5 to 10 different nucleotides and 1 mM or higher of Kd to MabBC200-A3 antibody (FIG. 14 and FIG. 15). Because the RNA binding affinity of four clones are lower than that of RNA (51-120), the present inventors determined that 4 clones did not have an affinity to the antibody, and confirmed that RNA (51-120) was only RNA being capable of binding to the antibody among the RNA pools.

The result of SELEX confirmed that 11 nucleotides were important in determination of antibody specificity.

Figure 16:
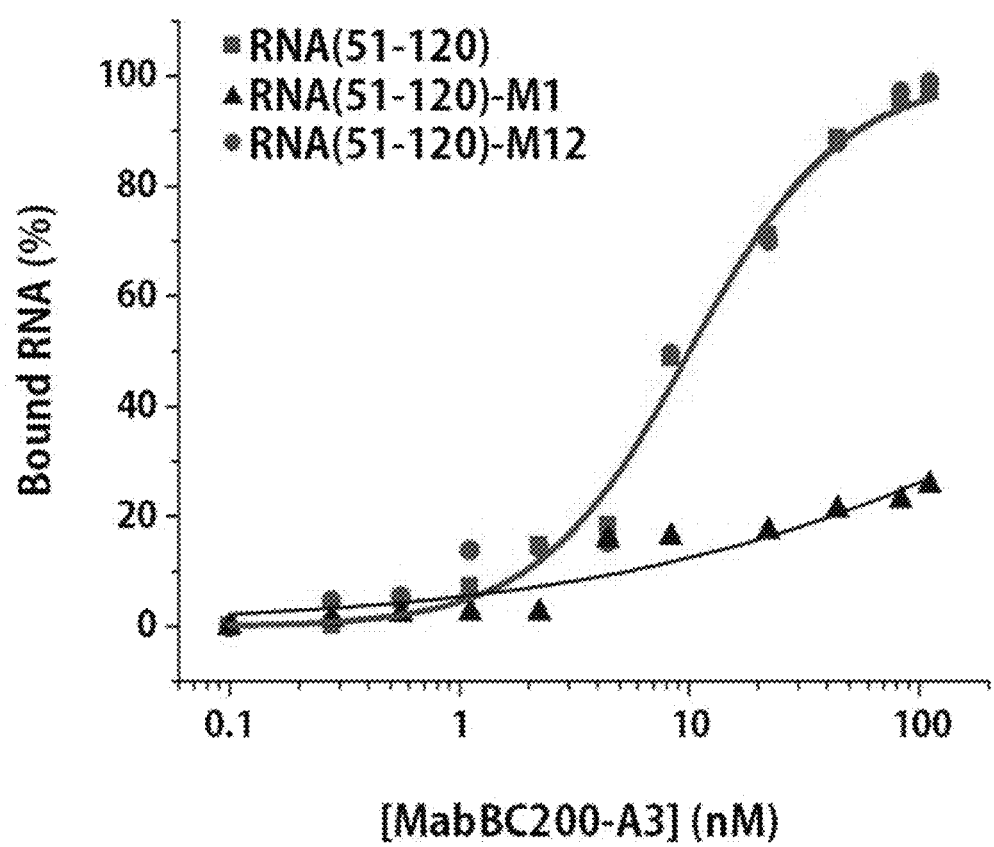
FIG. 16 shows the binding method for obtaining the dissociation constant of RNA (51-120) and its derivatives.

To investigate the need of specific structure of BC200 RNA for binding to the antibody, the mutant of RNA (51-120) was prepared for preventing the structure formation of RNA (51-120) by mutating the RNA for inhibiting the complementary binding of 71~77$^{th}$ nucleotides and 91~97$^{th}$ nucleotides which play an important role in the formation of RNA structure. CCA at 73~75$^{th}$ positions was changed into GGU in RNA (51-120), and named as RNA (51-120)-M1. As a result of binding affinity test of RNA (51-120)-M1, it did not bind to the antibody. However, RNA (51-120)-M12 which recover the complementary binding by reverse mutation on RNA (51-120)-M1 showed the equal binding affinity to RNA (51-120) (FIG. 16). The result suggested that the RNA structure was also important for antibody-RNA binding.

Figure 17:
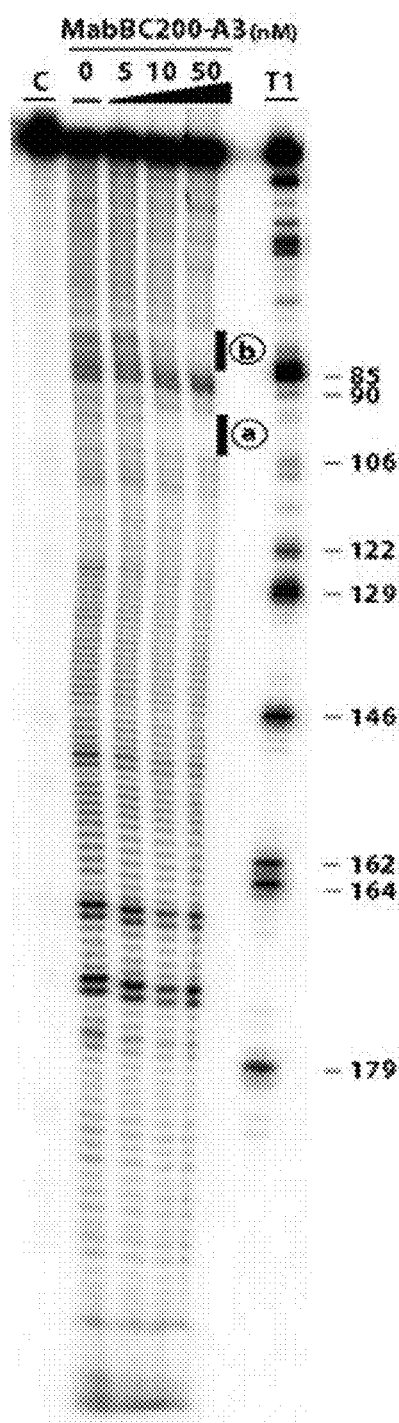
FIG. 17 shows the binding region of BC200 RNA with MabBC200-A3 using the hydroxyl radical foot-printing at concentrations of 0, 5, 10, and 50 nM of MabBC200-A3.
Figure 18:
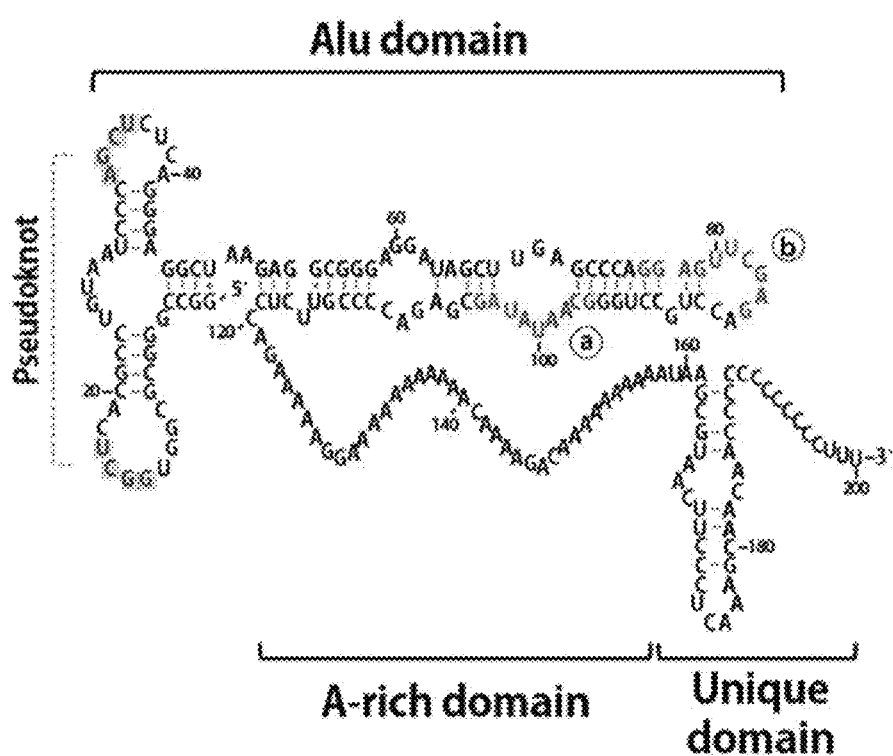
FIG. 18 shows a region of BC200 RNA binding to the antibody.
Figure 19:
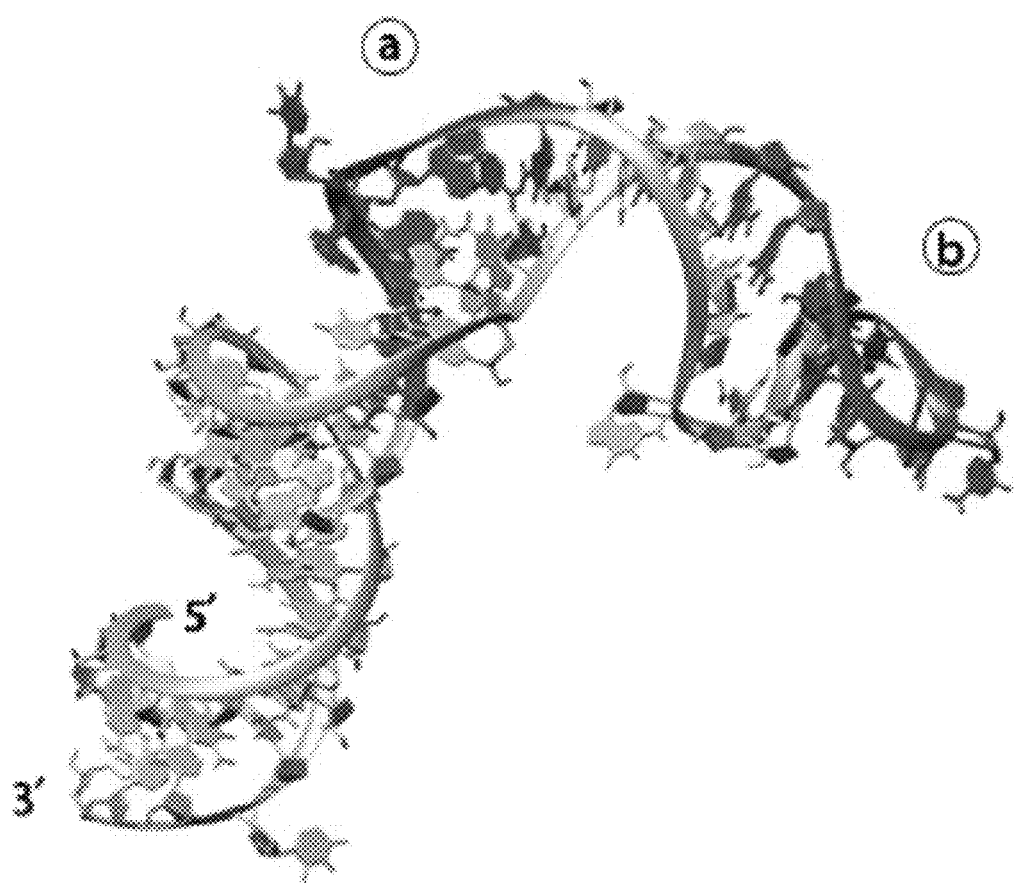
FIG. 19 shows a predicted tertiary structure of 51th to $119^{th}$ nucleotide sequence including the antibody-binding region among the BC200 RNA structure.

The present inventors confirmed that two regions of BC200 RNA, i.e., 76 to 85$^{th}$ nucleotides (SEQ ID NO: 11, ggaguucgag) and 96$^{th}$ to 104$^{th}$ nucleotides (SEQ ID NO: 12, gcaauauag) were protected by the antibody. In the secondary structure of BC200 RNA, two regions stayed away each other by a half of helix, and faced to the same direction in the predicted tertiary structure, when binding to the antibody. Because other parts except for the two regions were not changed in the footprinting method, the structure of BC200 RNA did not change, when binding to the antibody (FIGS. 17 to 19).

Example 10

Test of Antibody Binding to BC200 RNA 10.1 Total Amount of RNA Using Northern Blot Analysis To investigate that the ability of MabBC200-A3 can differentiate effectively RNA, total RNA of breast cancer cell line were used. Firstly, the amount of BC200 RNA in the breast cancer cell line was determined by using the northern blot analysis. Total cellular RNA was extracted from the cell by using Easy-Blue kit and was performed by electrophoresis using 7M urea and 6% PAGE and transferred to Hybond-XL membrane. The conjugation process was carried out by using the oligonucleotide which contained the nucleotide sequence complimentary to the BC200 RNA and was labeled with $^{32}$P at 5-terminus.

Figure 20:
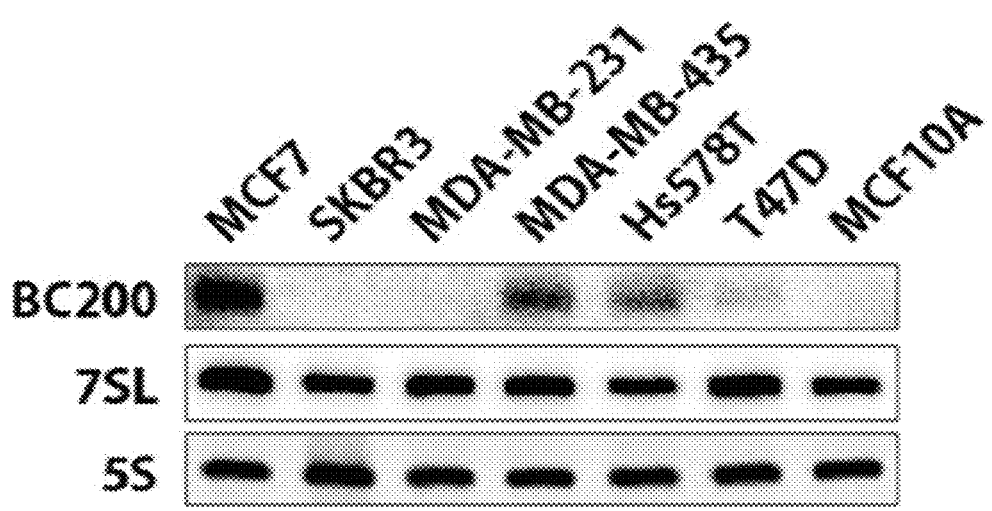
FIG. 20 shows a result of Northern blotting analysis for determining an amount of BC200 RNA among total cellular RNAs in breast cancer cell lines (MCF7, SKBR3, MDA-MB-231, MDA-MB-435, Hs578T and T47D), and in breast cell line of MCF10A.

7SL RNA and 5S RNA were detected with 7SL complementary oligonucleotide (SEQ ID NO: 34; 5'-GAGGTCAC-CATATTGATGCCGAACTTAGTG) labeled by 32P at 5'-terminus, and 5S complementary oligonucleotide (SEQ ID NO: 35; 5'-CATCCAAGTACTAACCAGGCCC) labeled by 32P at 5'-terminus. The membrane was analyzed according to the same method as described above. As an analysis result, the amounts of BC200 RNA were various in the cell lines, and were in order of MDA-MB-231=SKBR3<T47D<Hs578T<MDA-MB-435<MCF7. BC200 RNA was not discovered in DA-MB-231, SKBR3 or MCF10A of general breast cell line (FIG. 20).

10.2 the Test of Antibody Binding with BC200 RNA Using Immuno-Precipitation

Figure 21:
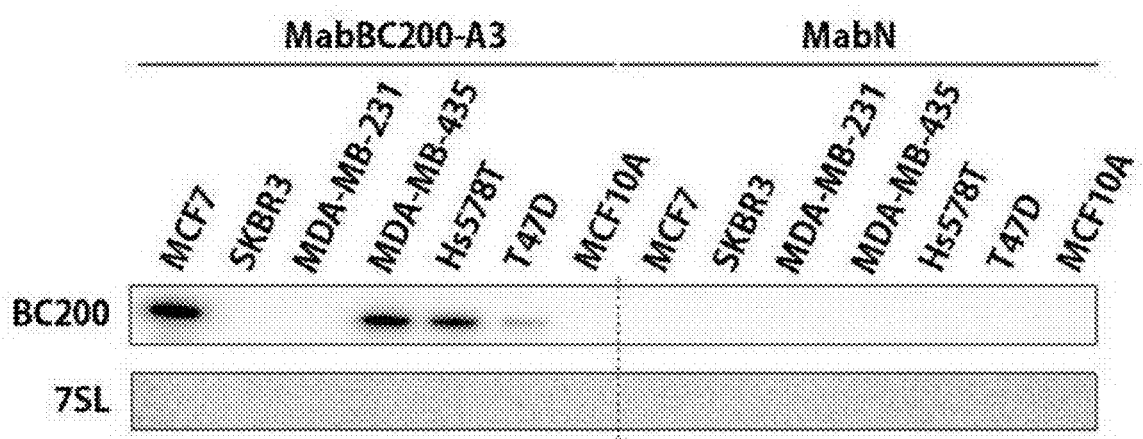
FIG. 21 shows a result of Northern blotting analysis for determining an amount of BC200 RNA immune-precipitated with MabBC200-A3 (MabN: negative control).

The cells washed with cooled PBS were suspended in PBS containing 10% fetal bovine serum and were fixed with 0.1% formaldehyde at a room temperature for 15 minutes. The cell permeability was increased in PBS containing 0.1% Tween-20 and reacted with MabBC200-A3 at a room temperature for 30 minutes. In the process, the cells were washed twice with cooled PBS at each step. The cells were reacted in cool RIPA solution (150 mM NaCl, 1% Sodium deoxycholate), 0.1% SDS, 1% Triton X-100, 2 mM EDTA, and 50 mM Tris-HCl, pH 7.5) and were performed continuously on ice for 30 minutes. Then, the reaction product was centrifuged at 16,000 g for 20 minutes. The immuneprecipitation was performed for the cell lysate of supernatant by using protein G. The amounts of BC200 RNA and 7SL RNA in the immune-precipitate were analyzed with Northern blot analysis. The whole cell lysate was processed according to the same method of the cell treatment, except for the antibody treatment. To measure the amount of antibody added to the cells, the cell lysate was analyzed with Western blot analysis, except for the final washing step. In summary, the purified RNA was reacted with MabBC200-A3 in 50 µl PBS for 30 minutes, and immuno-precipitated using protein G. The immuno-precipitate was extracted according to the phenol extraction method, and the amount of BC200 RNA was analyzed according to Northern blot method. As a result, unlike the negative antibody, BC200 RNA in the cells expressing BC200 RNA was immune-precipitated by using MabBC200-A3. 7SL RNA is a component of SRP (signal recognition particle) and a precursor of Alu, and is a majority of transposable elements (TE) in human genome. 5'-Alu domain of BC200 RNA showed the high conserved sequences with 7SL RNA. The region of BC200 RNA binding to MabBC200-A3 was located in Alu domain, but 7SL RNA was not immune-precipitated with the antibody. In this regard, MabBC200-A3 recognized specifically to only BC200 RNA (FIG. 21).

10.3 the Binding of Antibody with BC200 RNA Using the Flow Cytometry

Figure 22:
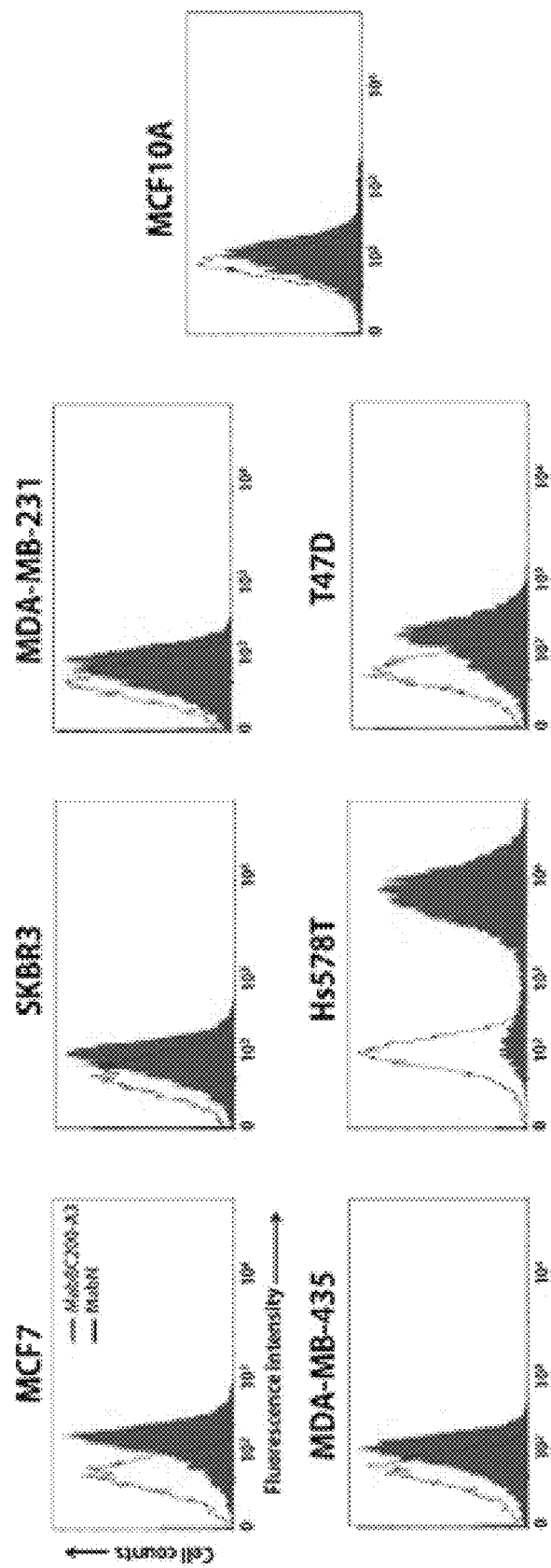
FIG. 22 shows a result of flow cytometry analysis of the sample treated with anti-human IgG attached to MabBC200-A and FITC.
Figure 23:
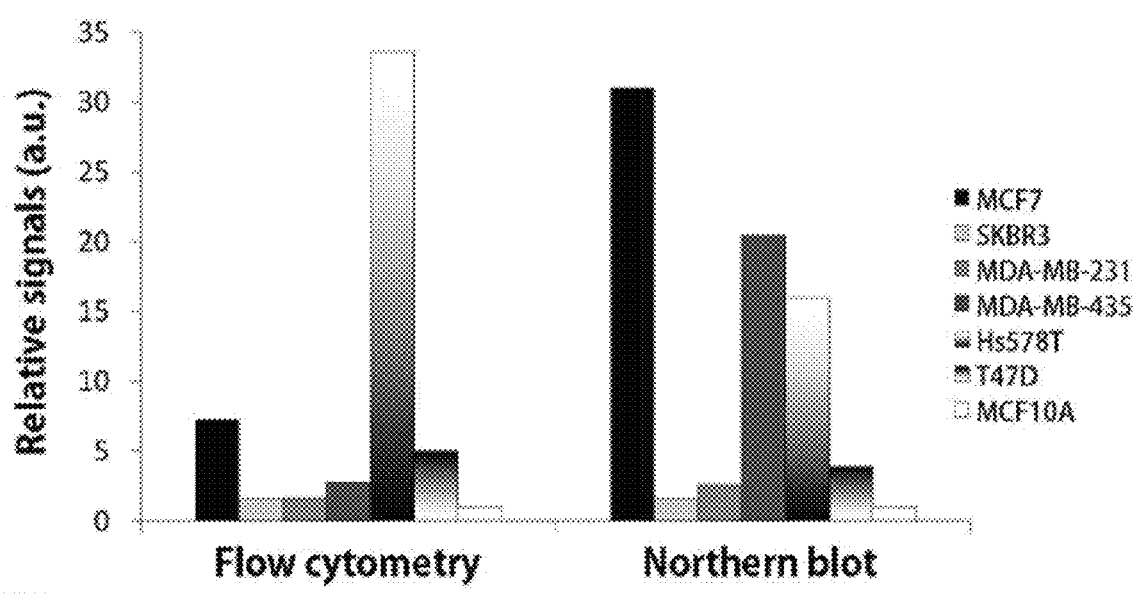
FIG. 23 is a graph comparing the fluorescence of flow cytometry method in FIG. 22 with the result of Northern blotting analysis in FIG. 20, where the flow cytometry method and Northern blotting analysis were normalized with MabN or 5S respectively, and the relative signal were shown by the value being proportional to the cell (arbitrary unit).
Figure 24:
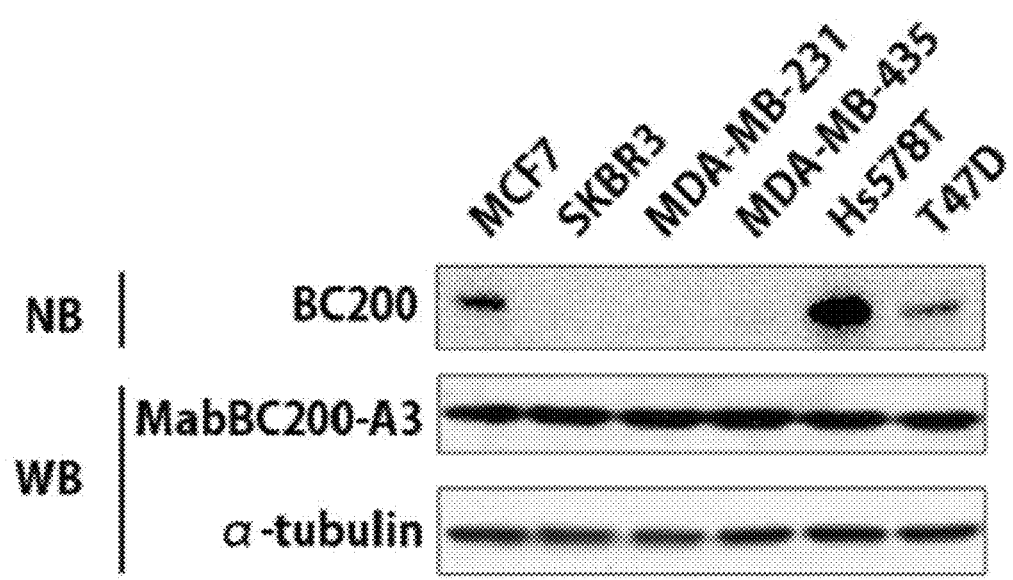
FIG. 24 shows a result of Northern blotting analysis for determining an amount of BC200 RNA in the cell lysate treated with MabBC200-A3 and immune-precipitated.
Figure 25:
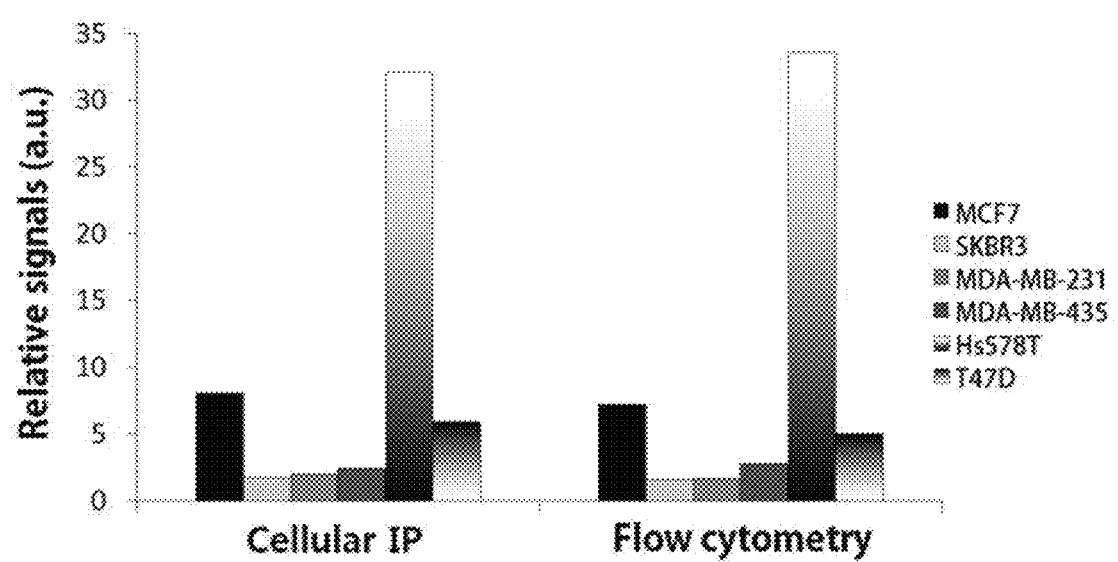
FIG. 25 is a graph comparing the result of Northern blotting analysis for the immuno-precipitation, with the fluorescence of flow cytometry method in FIG. 22.
Figure 26:
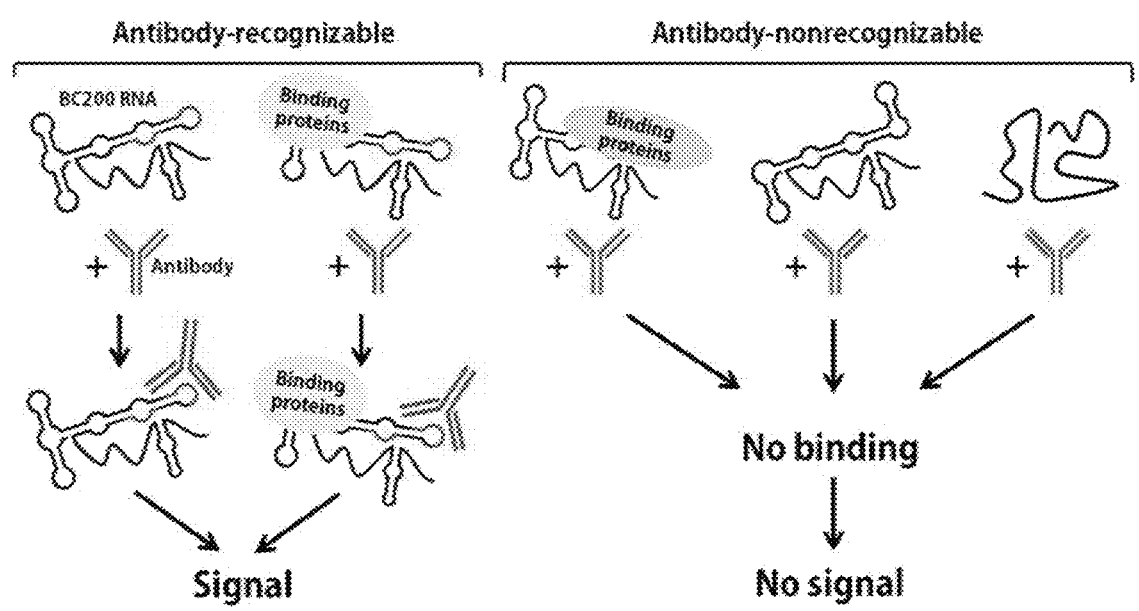
FIG. 26 shows a human anti-RNA antibody recognizing a specific structural motif of BC200 RNA.

To test that MabBC200-A3 can recognize BC200 RNA in a cell, the flow cytometry was carried out by using MabBC200-A3 a first antibody (FIG. 22). The cell preparation and the treatment of first antibody were performed according to the same method of immuno-precipitation in Example 9.2. Then, the cell was treated in the dark for 30 minutes with anti-human IgG labeled with fluorescein isothiocyanate (FITC) as a secondary antibody. The treated cells were collected and filtrated with Strainer capped tubes, and the fluorescence was detected with LSRII flow cytometry detector (BD Science, USA). The detected result was shown in a graph by using Flowing software. The fluorescence intensity measured by the flow cytometry was different from that of northern blot analysis (FIG. 23). The signals of Northern blot analysis for the amount of cellular BC200 RNA were represented in order of T47D<Hs578T<MDA-MB-435<MCF7, but the fluorescence intensities measured by the flow cytometry were represented in order of MDA-MB-435<T47D<MCF7<Hs578T. To investigate that the fluorescence intensities of flow cytometry was derived from BC200 RNA-antibody complex, BC200 RNA-antibody complex was immune-precipitated with cell lysate and the amount of BC200 RNA was analyzed with the northern blot (FIG. 24). In comparison of two results, the amount of immune-precipitated BC200 RNA was nearly the same as the intensity of flow cytometry (FIG. 25). The results suggested that BC200 RNA existed in two different forms where one form was recognized with MabBC200-A3 and the other form was not recognized with the antibody. Interestingly, MDA-MB-435 and Hs578T without expressing estrogen expressed similar amount of BC200 RNA, but had different amount of BC200 RNA which was recognized by the antibody. That is, most of BC200 RNA in MDA-MB-435 could not be recognized by the antibody of the present invention, but the most amount of BC200 RNA in Hs578T was recognized by the antibody.

---

What is claimed is:

1. An antibody or its antigen binding fragment, which binds specifically to a region of 50$^{th}$ nucleotide to 120$^{th}$ nucleotide in the nucleotide sequence of a brain cytoplasmic 200 (BC200) RNA having SEQ ID NO: 13
wherein the antibody or its antigen binding fragment comprises:
a variable region of heavy chain (V$_H$) comprising an complementarity region (CDR1) consisting of the amino acid sequence of SEQ ID NO: 1, CDR2 consisting of the amino acid sequence of SEQ ID NO: 2, and CDR3 consisting of the amino acid sequence of SEQ ID NO: 3; and,
a variable region of light chain (V$_L$) comprising CDR1 consisting of the amino acid sequence of SEQ ID NO: 4, CDR2 consisting of the amino acid sequence of SEQ ID NO: 5, and CDR3 consisting of the amino acid sequence of SEQ ID NO: 6, wherein serine (S) at the fourth position in the amino acid sequence of SEQ ID NO: 6 is substituted with another amino acid.

2. The antibody or its antigen binding fragment according to claim 1, wherein the antibody or its antigen binding fragment binds specifically to a region of SEQ ID NO: 11 or SEQ ID NO: 12 in a nucleotide sequence of BC200 RNA.

3. The antibody or its antigen binding fragment according to claim 1, wherein the CDR3 in variable region of light chain (V$_L$) consists of the amino acid sequence of SEQ ID NO: 6, wherein serine (S) at the fourth position in the amino acid sequence of SEQ ID NO: 6 is substituted with Glycine (G), Alanine (A), Cysteine (C) or Valine (V).

4. The antibody or its antigen binding fragment according to claim 1, wherein the CDR3 in variable region of light chain (V$_L$) consists of the amino acid sequence of SEQ ID NO: 7.

5. The antibody or its antigen binding fragment according to claim 1, wherein the CDR3 in variable region of light chain (V$_L$) consists of the amino acid sequence of SEQ ID NO: 8.

6. The antibody or its antigen binding fragment according to claim 1, wherein the CDR3 in variable region of light chain (V$_L$) consists of the amino acid sequence of SEQ ID NO: 9.

7. The antibody or its antigen binding fragment according to claim 1, wherein the CDR3 in variable region of light chain (V$_L$) consists of the amino acid sequence of SEQ ID NO: 10.

8. A method of detecting a brain cytoplasmic 200 (BC200) RNA in a sample, comprising a step of reacting an antibody or its antigen binding fragment as set forth in claim 1, with the sample.

9. The method according to claim 8, wherein the method further comprises a step of detecting whether the antibody or its antigen binding fragment binds specifically to the region of 50$^{th}$ nucleotide to 120$^{th}$ nucleotide in the nucleotide sequence of a brain cytoplasmic 200 (BC200) RNA having SEQ ID NO:13.

10. The method according to claim 8, wherein the antibody or its antigen binding fragment binds specifically to the region of SEQ ID NO: 11 or SEQ ID NO: 12 in a nucleotide sequence of BC200 RNA.

11. The method according to claim 10, wherein the CDR3 in the variable region of the light chain (V$_L$) consists of the amino acid sequence of SEQ ID NO: 6, wherein serine (S) at the fourth position in the amino acid sequence of SEQ ID NO: 6 is substituted with Glycine (G), Alanine (A), Cysteine (C) or Valine (V).

12. The method according to claim 10, wherein the CDR3 in variable region of light chain (V$_L$) consists of the amino acid sequence of SEQ ID NO: 7, 8, 9 or 10.

* * * * *